(12) United States Patent
Dando et al.

(10) Patent No.: US 8,043,288 B2
(45) Date of Patent: Oct. 25, 2011

(54) VIRTUAL ELECTRODE ABLATION CATHETER WITH ELECTRODE TIP AND VARIABLE RADIUS CAPABILITY ACTUATED WITH AT LEAST ONE RACK AND PINION MECHANISMS

(75) Inventors: Jeremy D. Dando, Plymouth, MN (US); Gregory J. Kampa, Castaic, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 852 days.

(21) Appl. No.: 11/617,524

(22) Filed: Dec. 28, 2006

(65) Prior Publication Data
US 2008/0161790 A1 Jul. 3, 2008

(51) Int. Cl.
*A61B 18/18* (2006.01)

(52) U.S. Cl. ............................................. 606/41

(58) Field of Classification Search ............ 606/41, 606/4
See application file for complete search history.

(56) References Cited

U.S. PATENT DOCUMENTS

| | | | | |
|---|---|---|---|---|
| 5,364,351 A * | 11/1994 | Heinzelman et al. | ...... | 604/95.04 |
| 5,395,327 A * | 3/1995 | Lundquist et al. | ........... | 604/528 |
| 5,395,329 A | 3/1995 | Fleischhackor et al. | | |
| 5,441,483 A * | 8/1995 | Avitall | ....................... | 604/95.05 |
| 5,626,136 A | 5/1997 | Webster, Jr. | | |
| 5,904,667 A * | 5/1999 | Falwell | ...................... | 604/95.01 |
| 5,935,102 A | 8/1999 | Bowden et al. | | |
| 6,033,397 A * | 3/2000 | Laufer et al. | .................... | 606/27 |
| 6,080,151 A | 6/2000 | Swartz et al. | | |
| 6,264,654 B1 | 7/2001 | Swartz et al. | | |
| 6,628,976 B1 | 9/2003 | Fuimaono et al. | | |
| 6,711,428 B2 | 3/2004 | Fuimaono et al. | | |
| 6,795,721 B2 | 9/2004 | Coleman et al. | | |
| 6,804,545 B2 | 10/2004 | Fuimaono et al. | | |
| 6,845,257 B2 | 1/2005 | Fuimaono et al. | | |
| 6,960,207 B2 | 11/2005 | Vanney et al. | | |
| 6,984,232 B2 | 1/2006 | Vanney et al. | | |
| 6,987,996 B2 | 1/2006 | Fuimaono et al. | | |
| 7,099,711 B2 | 8/2006 | Fuimaono et al. | | |
| 7,123,951 B2 | 10/2006 | Fuimaono et al. | | |
| 7,142,903 B2 | 11/2006 | Rodriguez et al. | | |
| 7,181,262 B2 | 2/2007 | Fuimaono et al. | | |
| 7,187,963 B2 | 3/2007 | Coleman et al. | | |
| 7,419,477 B2 * | 9/2008 | Simpson et al. | ........... | 604/95.04 |
| 2004/0034348 A1 * | 2/2004 | Rashidi | ........................... | 606/41 |
| 2004/0143255 A1 * | 7/2004 | Vanney et al. | .................. | 606/41 |
| 2007/0016164 A1 * | 1/2007 | Dudney et al. | ................ | 604/523 |

OTHER PUBLICATIONS

Biosense Webster "Lasso 2515 Variable Circular Catheter," http://www.biosensewebster.com/products/diagnostic/lasso.aspx. Printed Sep. 7, 2007, 2 pages.
St. Jude "Livewire TC Ablation Catheters," http://www.sjm.com/devices/device.aspx?name=Livewire+TC%26%23153%3b+Ablation+Catheters &location=us&type=12. Printed Sep. 7, 2007, 1 page.

* cited by examiner

*Primary Examiner* — Linda C Dvorak
*Assistant Examiner* — Benjamin Lee
(74) *Attorney, Agent, or Firm* — Trenner Law Firm LLC

(57) ABSTRACT

A cardiac ablation catheter system incorporates several different, but complementary features. The catheter includes a virtual electrode section for transferring ablation energy to form a linear lesion in cardiac tissue. The distal tip of the catheter shaft is provided with a tip electrode to perform spot ablations. The distal end of the catheter, generally including the virtual electrode section, may be operably formed into a curve with a variable radius of curvature.

26 Claims, 17 Drawing Sheets

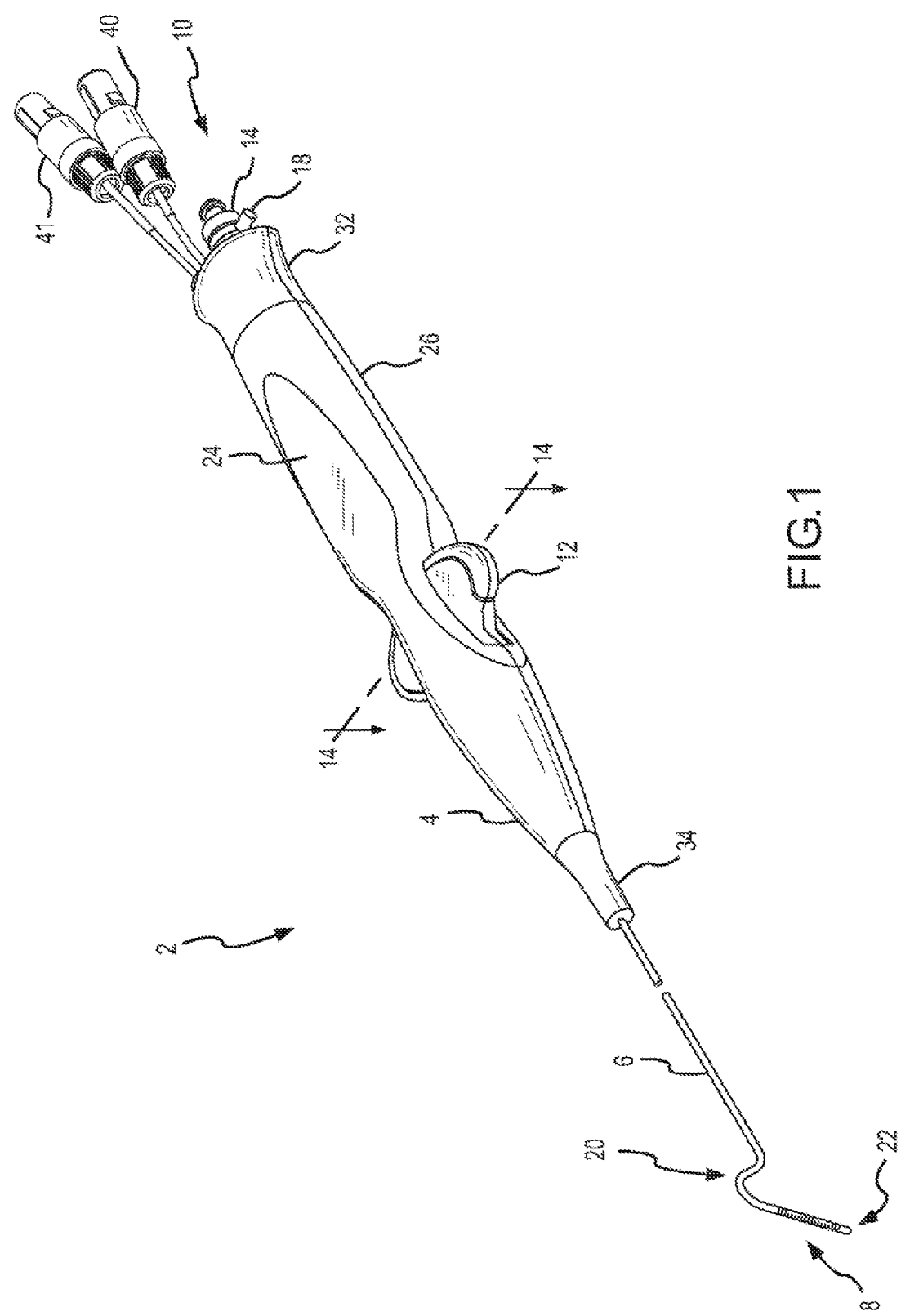

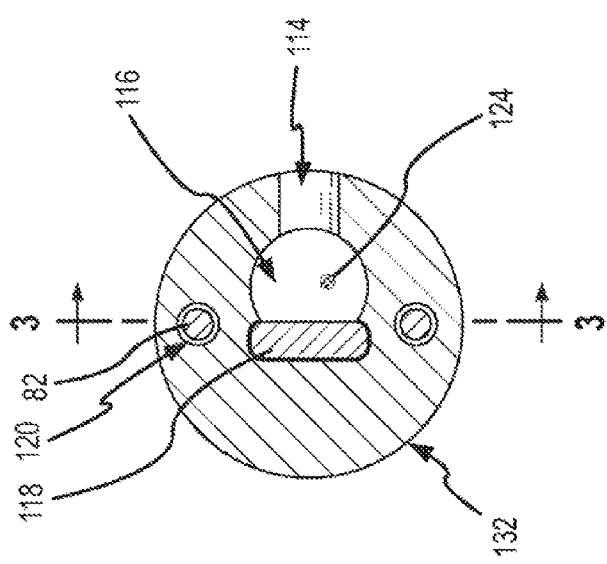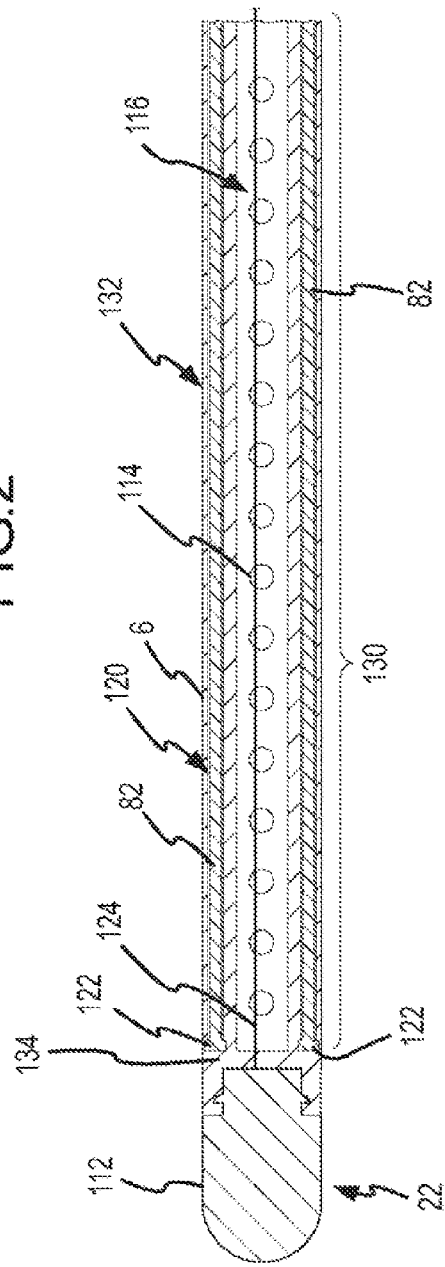

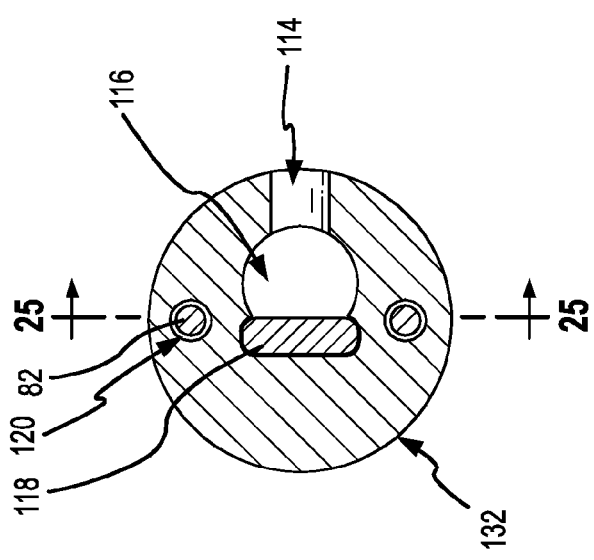
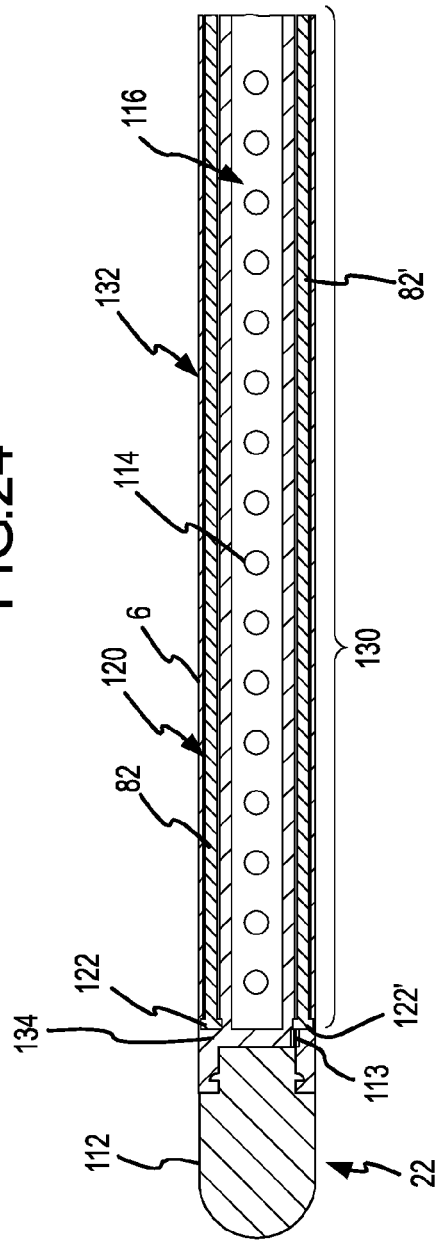
FIG.24
FIG.25

VIRTUAL ELECTRODE ABLATION CATHETER WITH ELECTRODE TIP AND VARIABLE RADIUS CAPABILITY ACTUATED WITH AT LEAST ONE RACK AND PINION MECHANISMS

BACKGROUND OF THE INVENTION a. Field of the Invention

The invention disclosed herein is directed toward an ablation catheter including a virtual electrode section that dispenses energized conductive fluid for ablation of tissue. The present invention also includes a system for deflecting or curving the distal end of the catheter.

b. Background Art

A catheter is generally a very small diameter tube for insertion into the body for the performance of medical procedures. Among other uses, catheters can be used to examine, diagnose, and treat disease while positioned at a specific location within the body that is otherwise inaccessible without more invasive procedures. During these procedures a catheter is inserted into the patient's vasculature near the surface of the body and is guided to a specific location within the body for examination, diagnosis, and treatment. For example, one procedure utilizes a catheter to convey an electrical stimulus to a selected location within the human body. Another procedure utilizes a catheter with sensing electrodes to monitor various forms of electrical activity in the human body.

In a normal heart, contraction and relaxation of the heart muscle (myocardium) takes place in an organized fashion as electrochemical signals pass sequentially through the myocardium from the sinoatrial (SA) node located in the right atrium, to the atrialventricular (AV) node in the septum between the right atrium and right ventricle, and then along a well-defined route which includes the His-Purkinje system into the left and right ventricles. Sometimes abnormal rhythms occur in the atria which are referred to as atrial arrhythmia. Three of the most common arrhythmia are ectopic atrial tachycardia, atrial fibrillation, and atrial flutter. Arrhythmia can result in significant patient discomfort and even death because of a number of associated problems, including the following: (1) an irregular heart rate, which causes a patient discomfort and anxiety; (2) loss of synchronous atrioventricular contractions, which compromises cardiac hemodynamics and results in varying levels of congestive heart failure; and (3) stasis of blood flow, which increases the vulnerability to thromboembolism.

It is sometimes difficult to isolate a specific pathological cause for the arrhythmia although it is believed that the principal mechanism is one or a multitude of stray circuits within the left and/or right atrium. These circuits or stray electrical signals are believed to interfere with the normal electrochemical signals passing from the SA node to the AV node and into the ventricles. Efforts to alleviate these problems in the past have included the use of various drugs. In some circumstances drug therapy is ineffective and frequently is plagued with side effects such as dizziness, nausea, vision problems, and other difficulties.

An increasingly common medical procedure for the treatment of certain types of cardiac arrhythmia and atrial arrhythmia involves the ablation of tissue in the heart to cut off the path for stray or improper electrical signals. The particular area for ablation depends on the type of underlying arrhythmia. Originally, such procedures actually involved making incisions in the myocardium (hence the term ablate, which means to cut) to create scar tissue that blocked the electrical signals. These procedures are now often performed with an ablation catheter. Typically, the ablation catheter is inserted in an artery or vein in the leg, neck, or arm of the patient and threaded, sometimes with the aid of a guide wire or introducer, through the vessels until a distal tip of the ablation catheter reaches the desired location for the ablation procedure in the heart. The ablation catheters commonly used to perform these ablation procedures apply electrical energy to the areas of the myocardial tissue to produce lesions and electrically isolate or render the tissue non-contractile. The lesion partially or completely blocks the stray electrical signals to lessen or eliminate arrhythmia.

One difficulty in obtaining an adequate ablation lesion using conventional ablation catheters is the constant movement of the heart, especially when there is an erratic or irregular heart beat. Another difficulty in obtaining an adequate ablation lesion is caused by the inability of conventional catheters to obtain and retain uniform contact with the cardiac tissue across the entire length of the ablation electrode surface. Without such continuous and uniform contact, any ablation lesions formed may not be adequate.

It is well known that benefits may be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, when sufficiently deep lesions are formed at specific locations in cardiac tissue via coagulation necrosis, undesirable ventricular tachycardias and atrial flutter may be lessened or eliminated. "Sufficiently deep" lesions means transmural lesions in some cardiac applications.

It has been discovered that more effective results may be achieved if a linear lesion of cardiac tissue is formed. The term "linear lesion" as used herein means an elongate, continuous lesion, whether straight or curved, that blocks electrical conduction. The ablation catheters commonly used to perform these procedures produce electrically inactive or noncontractile tissue at a selected location by physical contact of the cardiac tissue with an electrode of the ablation catheter. Current techniques for creating continuous linear lesions in endocardial applications include, for example, dragging a conventional catheter on the tissue, using an array electrode, or using pre-formed curved electrodes. Curved electrodes have also been formed by guiding a catheter with an array electrode over a wire rail. The wire rail is formed as a loop, thus guiding the distal end of the catheter into a loop form as well. The array electrodes and curved electrodes are generally placed along the length of tissue to be treated and energized to create a lesion in the tissue contiguous with the span of electrodes along the curved or looped surface. Alternately, some catheter designs incorporate steering mechanisms to direct an electrode at the distal tip of the catheter. The clinician places the distal tip electrode of the catheter on a targeted area of tissue by sensitive steering mechanisms and then relocates the electrode tip to an adjacent tissue location in order to form a continuous lesion.

The effectiveness of these procedures depends on a number of variables including the position and contact pressure of the tip electrode of the ablation catheter against the cardiac tissue, the time that the tip electrode of the ablation catheter is placed against the tissue, the amount of coagulum that is generated as a result of heat generated during the ablation procedure, and other variables associated with a beating heart, especially an erratically beating heart. Unless an uninterrupted track of cardiac tissue is ablated, non-ablated tissue or incompletely ablated tissue may remain electrically active, permitting the continuation of the stray circuit that causes the arrhythmia. Conventional tip electrodes with adjacent ring electrodes are not preferred for this type of procedure, however, because of the high amount of energy that is necessary to ablate sufficient tissue to produce a complete linear lesion. Also, conventional ring electrode ablation may leave holes or gaps in a lesion, which can provide a pathway along which unwanted electrochemical signals can travel.

During conventional ablation procedures, the ablating energy is delivered directly to the cardiac tissue by an electrode on the catheter placed against the surface of the tissue to raise the temperature of the tissue to be ablated. This rise in tissue temperature also causes a rise in the temperature of blood surrounding the electrode. This often results in the formation of coagulum on the electrode, which reduces the efficiency of the ablation electrode. With direct contact between the electrode and the blood, some of the energy targeted for the tissue ablation is dissipated into the blood. To achieve efficient and effective ablation, coagulation of blood that is common with conventional ablation catheters should be avoided. This coagulation problem can be especially significant when linear ablation lesions or tracks are produced because such linear ablation procedures conventionally take more time than ablation procedures ablating only a single location.

Another particular difficulty encountered with existing ablation catheters is assurance of adequate tissue contact. Many catheters use rigid electrodes that do not always conform to the tissue surface, especially when sharp gradients and undulations are present, such as at the ostium of the pulmonary veins in the left atrium and the isthmus of the right atrium between the inferior vena cava and the tricuspid valve. Consequently, continuous linear lesions are difficult to achieve. With present rigid catheters of uniform construction, it can be quite difficult to maintain sufficient contact pressure until an adequate lesion has been formed. This problem is exacerbated on contoured or trabecular surfaces. If the contact between the electrode and the tissue cannot be properly maintained, a quality lesion is unlikely to be formed.

To address the coagulation concern, more recent designs of ablation electrodes transfer energy to the target tissue with a conductive fluid medium that passes over a standard metal electrode rather than contacting the standard electrode to the tissue. The fluid flow thus reduces the likelihood that coagulum will form on any of the surfaces of the electrodes. These so-called "virtual electrodes" also help reduce tissue charring because the fluid, while energized, also acts as a cooling heat transfer medium.

The information included in this background section of the specification, including any references cited herein and any description or discussion thereof, is included for technical reference purposes only and is not to be regarded subject matter by which the scope of the invention is to be bound.

BRIEF SUMMARY OF THE INVENTION

The present invention is directed to a cardiac ablation catheter system incorporating several different, but complementary features not previously found in a catheter system. First, the catheter is designed to include a virtual electrode section for transferring ablation energy to form a linear lesion in cardiac tissue. Second, the distal tip of the catheter shaft is provided with a tip electrode in order to easily perform spot ablations. Third, the distal end of the catheter, generally including the virtual electrode section, may be operably formed into a curve of variable length and with a variable radius of curvature.

In one embodiment of the invention, a catheter assembly comprises a control handle at a proximal end of the catheter assembly and a catheter shaft attached to the control handle and extending distally therefrom. A tip electrode is joined to a distal tip of the catheter shaft. Further a virtual electrode structure is provided within a distal end section of the catheter shaft and is positioned adjacent and proximal to the tip electrode. A fluid lumen is defined within the catheter shaft and extends distally into the distal end section. The fluid lumen is in fluid communication with the virtual electrode structure. A control mechanism is interconnected between the distal end section of the catheter and the control handle. When the control mechanism is actuated at the control handle, a portion of the distal end section of the catheter shaft is caused to form a curved section. When the control mechanism is further manipulated, the radius of the curved section is varied.

In another embodiment of the invention, a virtual electrode catheter system has a control handle at a proximal end of the catheter system with an actuation mechanism. A catheter shaft is attached to the control handle and extends distally therefrom. A portion of a distal end section of the catheter shaft is oriented in a plane transverse to a longitudinal orientation of the catheter shaft proximal to the distal end section. A tip electrode is joined to a distal tip of the catheter shaft. An array of apertures is defined within an exterior wall of the distal end section of the catheter shaft and is positioned adjacent and proximal to the tip electrode. A fluid lumen is defined within the catheter shaft extending distally into the distal end section of the catheter shaft. The fluid lumen is at least partially bounded within the distal end section by the exterior catheter wall. Further, the apertures in the exterior wall fluidly interface with the fluid lumen. A first electrode lead is coupled at a proximal end with the control handle and positioned at a distal end within the distal end section of the catheter shaft such that at least a portion of the first electrode lead is exposed to the interior of the fluid lumen. A second electrode lead is housed within the catheter shaft. The second electrode lead is coupled at a proximal end with the control handle and coupled at a distal end to the tip electrode. A first deflection wire is housed within the catheter shaft, connected at its proximal end with the actuator mechanism in the control handle, and anchored at its distal end within the catheter shaft at a first position proximal and adjacent to the tip electrode. A second deflection wire is housed within the catheter shaft, connected at its proximal end with the actuator mechanism in the control handle, and anchored at its distal end within the catheter shaft at a second position proximal and adjacent to the tip electrode.

Other features, details, utilities, and advantages of the present invention will be apparent from the following more particular written description of various embodiments of the invention as further illustrated in the accompanying drawings and defined in the appended claims.

BRIEF DESCRIPTION OF THE DRAWINGS

FIG. 1 is an isometric view of a catheter including a control handle and an ablation electrode section according to a generic embodiment of the present invention.

FIG. 2 is a cross-section view of the catheter of FIG. 1 taken along line 2-2 as indicated in FIG. 6.

FIG. 3 is a cross-section view of the catheter of FIG. 1 taken along line 3-3 as indicated in FIG. 2.

FIG. 24 is a cross-section view of a catheter according to an alternative embodiment taken along a line similar to line 2-2 as indicated in FIG. 6.

FIG. 25 is a cross-section view of the catheter of FIG. 24 taken along line 25-25 as indicated in FIG. 24.

DETAILED DESCRIPTION OF THE INVENTION

The present invention concerns an improved design for ablation catheters used, for example, in cardiac ablation procedures to produce lesions in cardiac tissue. The electrode structure on the distal end of the catheter of the present invention is generally termed a "virtual electrode." In a virtual electrode design, ablation energy is primarily imparted to the target tissue via energy transfer through a conductive fluid medium escaping the distal end of the catheter rather than by actual contact of a traditional electrode with the tissue. The present invention also combines a standard distal tip electrode with the virtual electrode structure to perform spot ablations as necessary. The present invention additionally provides a mechanism for manipulating the distal end of the catheter containing the electrode structure into curved shapes of variable lengths and radii.

Figure 6:
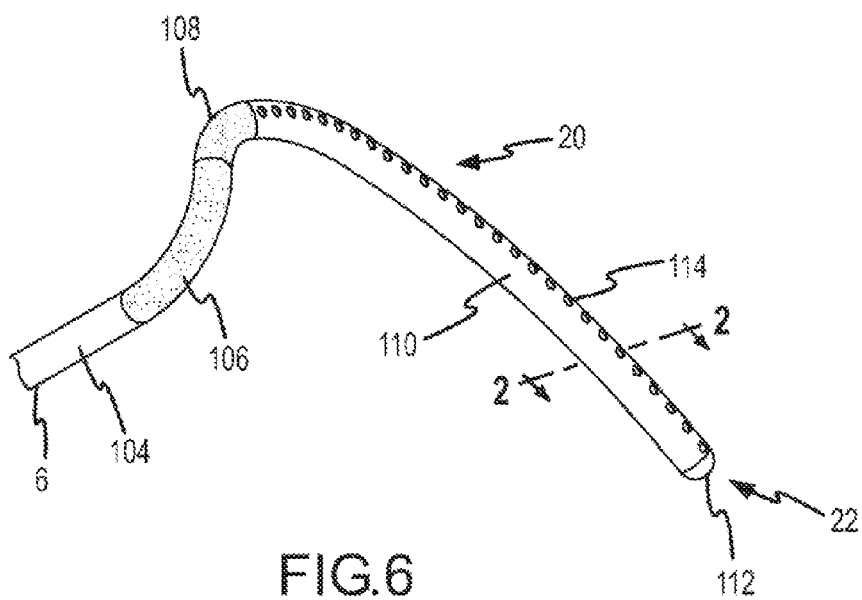
FIG. 6 is an isometric view of the distal view end of the catheter of FIG. 1 in a first configuration.
Figure 12:
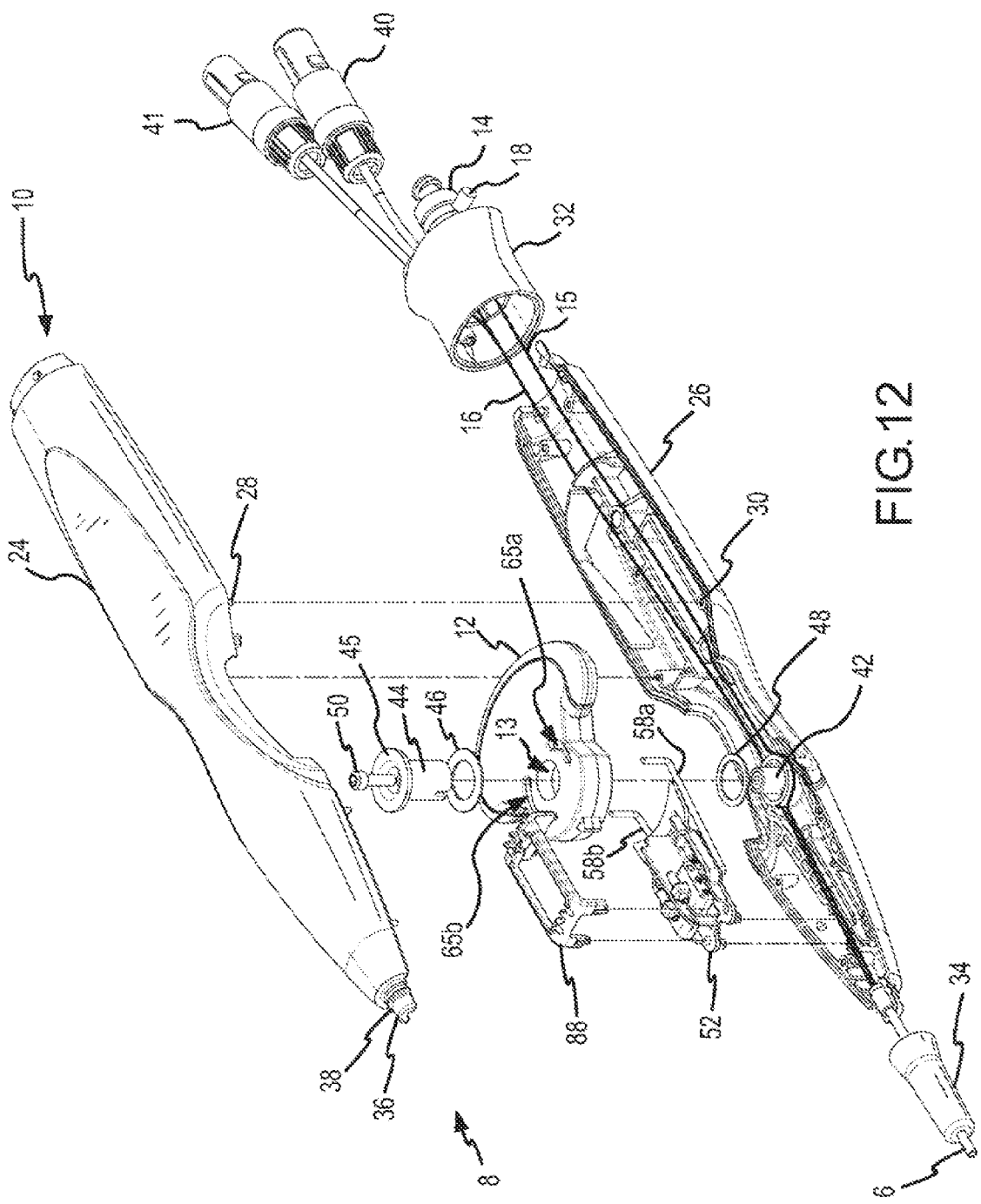
FIG. 12 is an exploded view of the control handle of the catheter assembly of FIG. 1.

FIG. 1 depicts a catheter assembly 2 for a variable radius virtual electrode catheter according to a generic embodiment of the present invention. The catheter assembly 2 includes a catheter shaft 6, which is attached to a control handle 4 adjacent the proximal end 10 of the catheter assembly 2. At a distal end 8 of the catheter assembly 2, the catheter shaft 6 includes an ablation electrode section 20. A distal tip 22 of the catheter 6 may further include a tip electrode 112 (see e.g., FIGS. 3 and 6). A hemostatic valve 14 is positioned at the proximal end 10 and connected via tubing 15 through the control handle 4 to catheter shaft 6 (e.g., as shown in FIG. 12). Control wires 16 may similarly be routed through the control handle 4. The hemostatic valve 14 forms a fluid-tight seal against the fluid lumen 116 (depicted in FIGS. 2 and 3) and prevents blood or other fluid that may fill the catheter shaft 6 from flowing proximally and entering a fluid source. Fluid source may include e.g., isotonic saline, other conductive fluid, or a drug, to easily introduce the fluid into the catheter 6, for example, to operate the ablation electrode section 20 as a virtual electrode 130 (see, e.g., FIG. 3) or to inject a drug in to the patient. The hemostatic valve 14 may have a port or other fluid introduction valve 18 which may be connected to the fluid source.

The structure of the ablation electrode section 20 is depicted in greater detail in FIGS. 2, 3, and 6-11. As previously indicated, the distal end 8 of the catheter assembly 2 forms the ablation electrode section 20. The ablation electrode section 20 is composed of both a virtual electrode structure 130 for creating a linear lesion and a tip electrode 112 at the distal tip 22 of the catheter shaft 6 for creating spot lesions. The virtual electrode section 130 is composed of a linear array of portholes 114 arranged longitudinally along the distal end 8 of the catheter shaft 6. The portholes 114 are apertures formed within the exterior wall 132 of the catheter shaft 62. A fluid lumen 116 is defined by the catheter shaft 6 and extends from at least the hemostatic valve 14 at a proximal end, distally through the ablation electrode section 20, and terminates adjacent to the distal tip 22 of the catheter shaft 6. The fluid lumen 116 is bounded on at least one side by the exterior wall 132 of the catheter shaft 6. Thus, the portholes 114 provide fluid communication from the fluid lumen 116 to the exterior of the catheter shaft 6 within the virtual electrode section 130.

A fluid electrode 118 extends within the fluid lumen 116 to transfer RF ablation energy from an energy source, e.g., an RF generator connected with the control coupling 40 and power connection 41 at the proximal end 10 of the catheter assembly 2 (e.g., FIG. 1), to the conductive fluid within the fluid lumen 116. The fluid electrode 118 thereby energizes the conductive fluid exiting the portholes 114. When the energized fluid contacts tissue adjacent to the virtual electrode section 130 of the catheter shaft 6, a linear lesion in the tissue may be formed. The fluid electrode 118 may be platinum, gold, or stainless steel wire, or other appropriate biocompatible metal conductor. The fluid electrode 118 is generally only exposed within the virtual electrode section 130, while the length of the fluid electrode 118 proximal to the virtual electrode section 130 is preferably electrically insulated from the conductive fluid in the fluid lumen 116. Alternatively, a separate electrode lead (not shown) may be housed within the catheter shaft 6 outside of the fluid lumen 116 and coupled with the fluid electrode 118 in the virtual electrode section 130.

As depicted in FIGS. 3 and 6-10, a tip electrode 112 is fixed to the distal end of the catheter shaft 6. The tip electrode may be formed of platinum, gold, stainless steel, or other biocompatible conductive metal. A tip electrode lead 124 may be threaded through the fluid lumen 116 from the control handle 4 to the distal tip 22 of the catheter shaft 6. The tip electrode lead 124 is insulated along its length until its distal end couples with the tip electrode 112. The tip electrode lead 124 may be made platinum, gold, stainless steel, or other biocompatible wire with an electrically insulating coating. As shown in FIG. 3, the tip electrode 112 is separated from the distal end 8 of the fluid lumen 116 by an end wall 134 of the catheter shaft 6. The end wall 134 both fluidly and electrically isolates the conductive fluid in the fluid lumen 116 from contact with the tip electrode 112. The end wall 134 similarly electrically isolates the fluid electrode 118 from the tip electrode 112. The distal end of the tip electrode lead 124 passes through the end wall 134 in order to electrically couple with the tip electrode 112. In this manner, both the tip electrode 112 and the fluid electrode 118 may be separately actuated. In an alternative embodiment, a common lead may energize both the tip electrode and the fluid electrode.

One or more deflection wires 82 may be additionally housed within the catheter shaft 6 as additionally shown in FIGS. 2 and 3. The deflection wires 82 are used to impart a curve of a varying radius to the ablation electrode section 20 of the catheter shaft 6 as described in greater detail below. The proximal end of each of the deflection wires 58 is attached via a control mechanism to the actuator 12 within the control handle 4 as further described herein with respect to FIGS. 12-15. The deflection wires 82 run the length of the catheter shaft 6, traveling distally from the control handle 4 to a point adjacent the end wall 134 at the distal tip 22 of the catheter shaft 6. The deflection wires 82 may be housed within separate deflection wire lumen 120 formed within and along the length of the catheter shaft 6, at least within the ablation electrode section 20. The deflection wire lumen 120 are generally positioned 180° apart within the ablation electrode section 20 adjacent to the exterior wall 132 of the catheter 6. The deflection wires 82 and deflection wire lumen 120 are further located outside of the fluid lumen 54 and are positioned 90° apart from the array of portholes 114.

The distal ends of the deflection wires 82 terminate at respective deflection wire anchors 122, which are embedded within the body of the catheter shaft 6 adjacent the end wall 134. The deflection wire anchors 122 ensure the distal ends of the deflection wires 82 remain in place adjacent the distal tip 22 of the catheter shaft 6. The positions of the deflection wires 82 within the catheter shaft 6 are designed to impart one or more curves to the ablation electrode section 20 of the catheter shaft 6 when either of the deflection wires 82 is under tension. For example, a curve created in the ablation electrode section 20 of the catheter shaft 6 may align the portholes 114 along a distal edge of the curve as described further below with respect to FIGS. 16A-21B.

In a first alternate embodiment (not shown) of an ablation electrode section for a catheter according the present invention, a coil electrode may be disposed within the fluid lumen within the virtual electrode section. The use of a coil electrode may allow for more efficient energy transfer of RF energy from the coil electrode to the conductive fluid within the fluid lumen. In a second alternate embodiment (see FIGS. 24 and 25), the deflection wire anchor 122' of one of the deflection wires 82' may be electrically coupled with the tip electrode 112 that is fixed to the distal tip 22 of the catheter shaft 6. The tip electrode 112 may be formed with a protruding pin 113 that physically connects with and is electrical coupled to the deflection wire anchor 122'. In this embodiment, the deflection wire 82' acts as the electrical lead to provide ablation energy to the tip electrode 112 via the coupling interface of the deflection wire anchor 122' and the tip electrode 112, thus obviating the need for a separate electrode lead to contact the tip electrode 112. In a third alternative embodiment (not shown), wherein there is no need for separate actuation of the fluid electrode and the tip electrode, the distal end of the fluid electrode (e.g., the flat electrode, the coil electrode, or any other form of a fluid electrode) may alternatively be electrically coupled with the tip electrode to energize the tip electrode as well as the conductive fluid.

As depicted in FIGS. 4 and 6-11, the catheter shaft 6 may be constructed from a number of different polymers, for example, polypropylene, oriented polypropylene, polyethylene, polyethylene terephthalate, crystallized polyethylene terephthalate, polyester, polyvinyl chloride, polytetraflouroethylene (PTFE), expanded polytetraflouroethylene (ePTFE), and Pellethane®, either individually or in combination. Alternatively, different sections of the catheter shaft 6 may be composed, for example, of different formulations of Pebax® resins (AUTOFINA Chemicals, Inc., Philadelphia, Pa.), or other polyether-block co-polyamide polymers, which can be used to create desired material stiffness within the different sections of the catheter shaft 6. By using different formulations of the Pebax® resins, different mechanical properties (e.g., flexibility or stiffness) can be chosen for different sections along the catheter shaft 6 if desired. For example, the majority of the length of the catheter shaft 6 may be formed of a stiffer polymer, while the distal end 8 that is manipulable may be formed of a more flexible polymer for ease of deflection.

Figure 4:
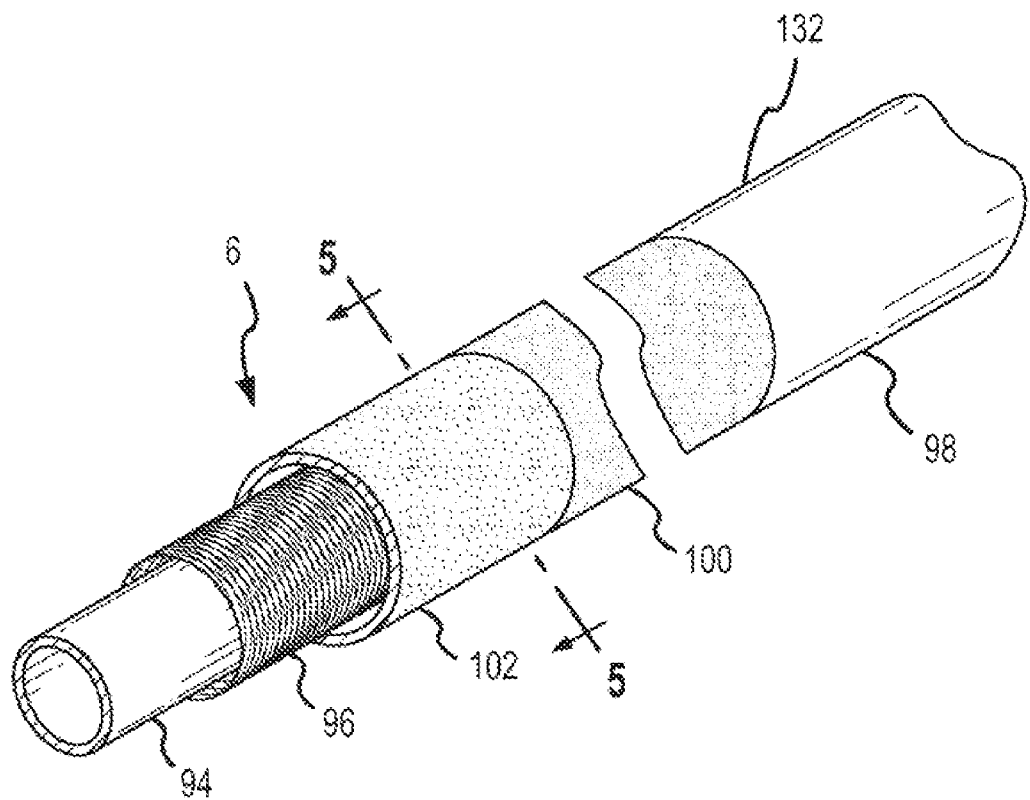
FIG. 4 is an expanded isometric view of a portion of the catheter of FIG. 1 depicting a construction of the catheter wall.
Figure 5:
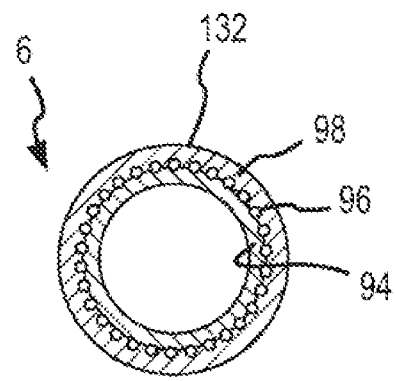
FIG. 5 is a cross-section view of the catheter of FIG. 1 taken along line 5-5 as indicated in FIG. 4.

As shown in FIGS. 4-11, the catheter shaft 4 may be component-built, i.e., formed from section of different materials. The catheter wall 132 may be formed of several layers of materials to ultimately create a composite structure. As shown in FIGS. 4 and 5 the catheter wall may be composed of an inner tube 94 of plastic, which is initially surrounded by a cylindrical braid 96 of metal fibers, for example, stainless steel fibers, which in turn is surrounded by one or more outer tubes of plastic material. The metallic braid 96 is included in the catheter wall to add stability to the catheter shaft 6 and also to resist radial forces that might crush the catheter shaft 6. The metallic braid 96 also provides a framework to translate torsional forces imparted by the clinician at the proximal end 10 of the catheter shaft 6 to the distal end 8 to rotate the catheter shaft 6 for appropriate orientation of the ablation electrode section 20. The choice of a flat, angled braid pattern for the metallic braid 96 as depicted adds hoop strength to the catheter shaft 6 without impacting the flexibility of the catheter shaft 6.

Based upon the exemplary configuration of FIG. 4, three collinear sections of equal diameter plastic tubing abutted together surround the metallic braid 96. A first tube 98 is composed of a first plastic material, a second tube 100 is composed of a second plastic material, and a third tube 102 is composed of a third plastic material. The inner tube 94 is generally chosen to have a relatively pliant material formulation. These component plastic sections of the catheter wall 132 may be composed, for example, of Pebax® resins (AUTOFINA Chemicals, Inc., Philadelphia, Pa.), or other polyether-block co-polyamide polymers, wherein different formulas are used to create the desired material stiffness within each section of the catheter wall 132. These sections of different material enable the catheter shaft 6 to have different mechanical properties (e.g., varying ranges of flexibility) at different locations along the catheter shaft 6.

For example, in order to form the curved shapes of the ablation section 20 of the catheter 6 as shown in FIGS. 6-11, the catheter wall 132 may be a composite construction as depicted in FIG. 4. The first curved section 106 may be formed by the first tube 102 having a relatively more pliant material formulation than the proximal straight section 104 of the catheter wall 132 to provide a level of suspension to the distal tip 22 as further described below. The second curved section 108 may be formed by the second tube 100, which may have a slightly stiffer formulation than the first tube 102. The third curved section 110 may be formed by the third tube 102 having a relatively more rigid material formulation to create greater stiffness than the second curved section 106 as well to provide appropriate support to the ablation electrode 20. The proximal straight section 104 of the catheter 6 may be formed of material having a relatively stiffer material formulation than the first section 106, allowing for greater transfer of control exerted at the proximal end of the catheter 4 to the distal end 8. In an exemplary embodiment, the first tube 74 may have a hardness of 72 Shore D, the second tube may have a hardness of 55 Shore D, the third tube may have a hardness of 65 Shore D, and the inner tube may have a hardness of 40 Shore D. The distal section 18 may further comprise a radiopaque marker to allow a clinician to visualize the position of the distal end 8 of the catheter 4 in the heart.

Once the appropriate material qualities of the plastic for each of the inner, first, second, and third tubes 94, 98, 100, 102 are chosen, the catheter wall 132 can be fabricated. As previously described, the inner tube 94 is first surrounded by the metallic braid 96. The first, second, and third tubes 98, 100, 102 are then placed around the metallic braid 96 and are abutted together, end-to-end. The first, second, and third tubes 98, 100, 102 may then be covered by a shrink wrap tube (not shown), if desired, to maintain the close abutment between the adjacent ends of the first, second, and third tubes 98, 100, 102. The layered structure of the inner tube 94, the metallic braid 96, the first, second, and third tubes 98, 10, 102, and the shrink wrap is then heated to a temperature at which the plastic materials composing each of the inner, first, second, and third tubes 94, 98, 100, 102 begin to melt. The plastic of the inner tube 94 flows through the interstices of the metallic braid 96 from the inside. Similarly, the plastic of the first, second, and third tubes 98, 100, 102 flows through the interstices of the metallic braid 96 from the outside. In this manner, the inner tube 94 is welded to the first, second, and third tubes 98, 100, 102, Thus, the metallic braid 96 is encapsulated between them to form the catheter wall 44 as shown in FIG. 5. Similarly, the adjacent ends of the first tube 98 and second tube 100 are welded together and the adjacent ends of the second tube 100 and the third tube 102 are welded together. If the shrink wrap tube is used, it encapsulates the entire catheter wall 132 of the component catheter 6.

As indicated above, the various sections of the catheter 6 may be provided with preset curves. Such curvature can be imparted to the catheter 4, for example, by placing a mandrel of a desired form in the catheter 6 and thermally setting the desired curvature to the catheter wall 132. Although the catheter wall 132 depicted in the figures (and as shown in cross-section in FIG. 5) has a circular cross section, the cross-section of the catheter wall 132 may be other than circular.

The distal end 8 of the catheter 6 comprising, at least in part, the ablation electrode section 20 may be straight or take on a myriad of shapes depending upon the desired application. The distal end 8 of several embodiments of the catheter 6 according to the present invention is shown in greater detail in FIGS. 6-11. In the embodiments shown, the catheter 6 consists mainly of a "straight" section 104 extending from the control handle 4 at the proximal end 10 to the distal end 8 of the catheter shaft 6 at a point adjacent to the ablation electrode section 20. The straight section 104 is generally the portion of the catheter 6 that remains within the vasculature of the patient while a clinician performs a sensing or ablation procedure. At the distal end 8, the catheter 6 is composed of a first curved section 106 and a second curved section 108 before transitioning into a third curved section 110 that begins the ablation electrode section 20. The first curved section 106 is adjacent and distal to the straight section 104 and proximal and adjacent to the second curved section 108. The second curved section 108 is itself proximal and adjacent to the third curved section 110.

Figure 7:
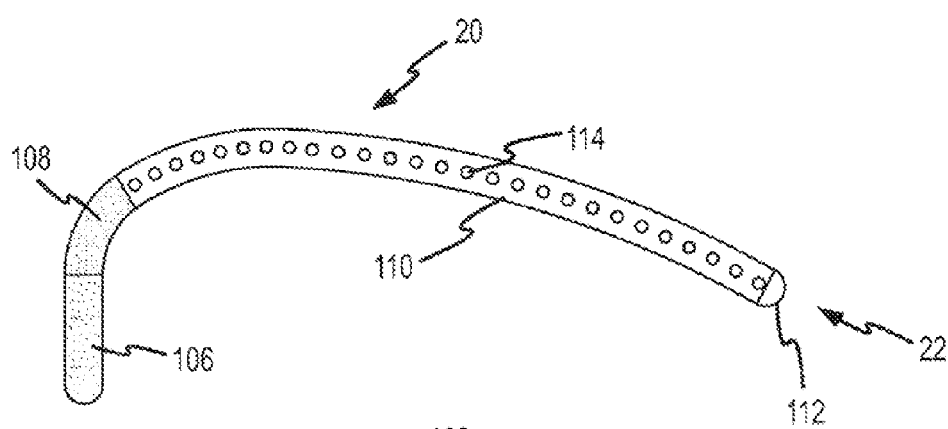
FIG. 7 is a distal plan view of the distal end of the catheter of FIG. 1 in the configuration of FIG. 6.
Figure 8:
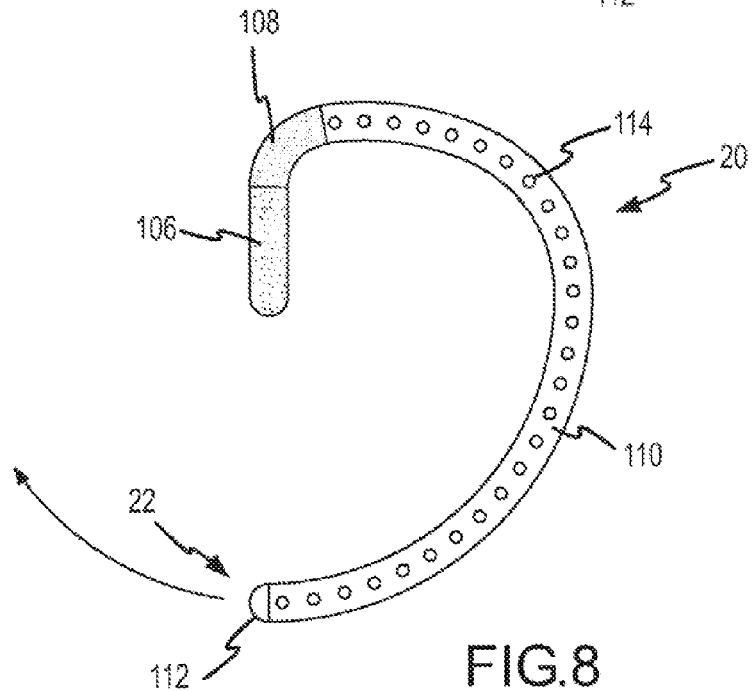
FIG. 8 is a distal plan view of the distal end of the catheter of FIG. 1 in a second configuration.

The straight section 104, first curved section 106, second curved section 108, and third curved section 110 may together form a single, unitary structure of the catheter 6, but may originally be separate pieces joined together to form the catheter 6. For example, as indicated above, each of the different sections of the catheter may be composed of different formulations of Pebax® resins, or other polyether-block co-polyamide polymers, which can be used to create desired material stiffness within the different sections of the catheter 6. By joining separate curved sections or unitarily molding the distal end of the catheter shaft 6 proximal to the ablation electrode section 20 using a relatively stiff resin, a desired shape can be imparted to that section of the catheter shaft 6 to effect the ultimate orientation of the ablation electrode section 20. For example, the third curve section 110 may be set with curves of varying radius to achieve any number of forms for examples as depicted in FIGS. 7-9.

Figure 9:
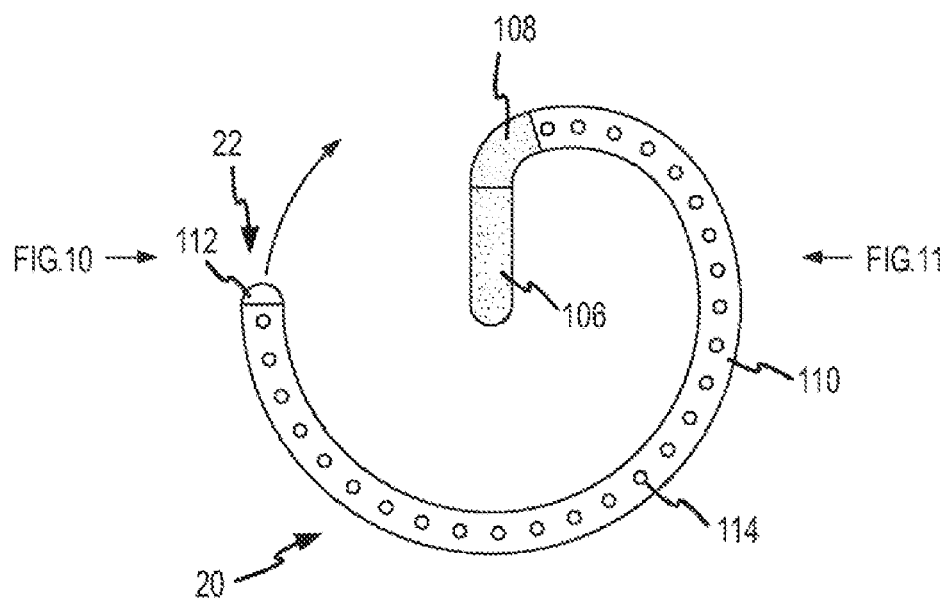
FIG. 9 is a distal plan view of the distal end of the catheter of FIG. 1 in a third configuration.
Figures 10, 11:
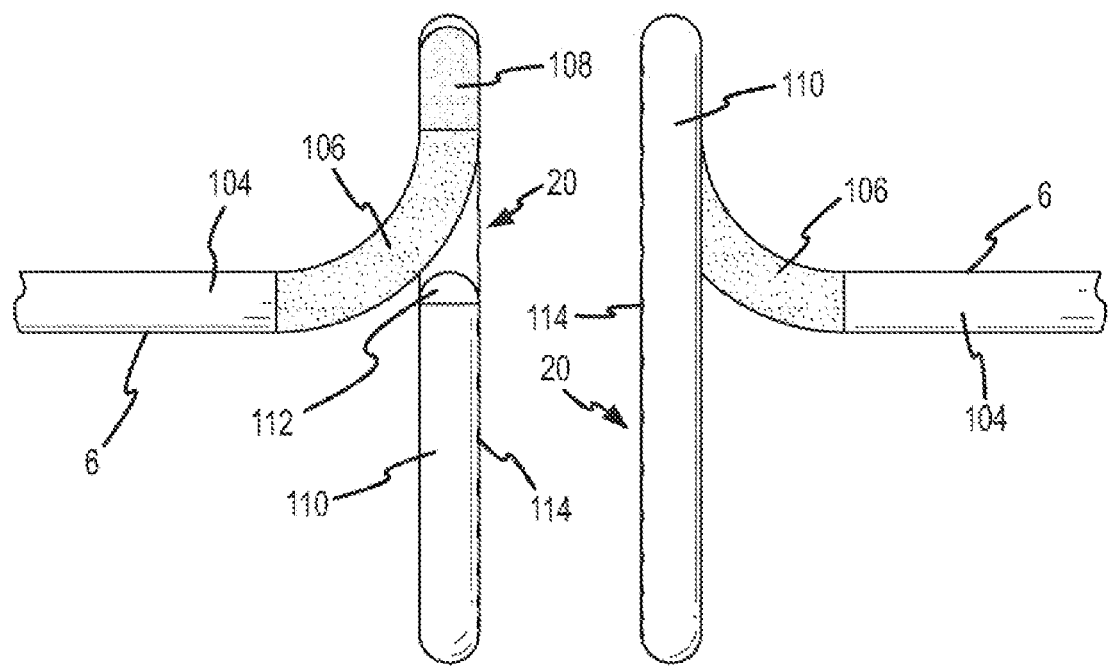
FIG. 10 is a side elevation view of the distal end of the catheter of FIG. 1 from the direction indicated in FIG. 9.
FIG. 11 is side elevation view of the distal end of the catheter of FIG. 1 from the direction indicated in FIG. 9.

As shown in FIGS. 6-11, the first curved section 106 and second curved section 108 of the catheter 6 align the third curved section 110 such that it lies in a plane transverse to the orientation of the straight section 104 of the catheter 22. In addition, the distal end 8 of the straight section 104 of the catheter 6 is oriented in a position where a longitudinal axis extending through the distal end of the straight section 112 is displaced from the curve of the third curved section 110. If the curves are so constructed, this longitudinal axis may pass orthogonally through substantially the center of a circle defined by the C-shaped third curved section 110 as depicted in FIG. 9. In this many the straight section 104 of the catheter 6 is spatially displaced from the ablation electrode section 20 so that the straight section 104 is unlikely to interface with the interface between the ablation electrode section 20 extending from the third curved section 110 and the cardiac tissue as further described below.

Returning attention to FIG. 1, the control handle 4 is encased by a top cover 24 and a bottom cover 26. The top cover 24 and the bottom cover 26 are secured together in part by a proximal cap 32 at the proximal end 10 of the control handle 4. A strain relief boot 34 is attached to the distal end 8 of the control handle 4 and similarly operates in part to hold the top cover 24 and the bottom cover 26 together as shown to better in advantage in FIG. 12. An actuator 12 is sandwiched between the top cover 24 and the bottom cover 26 slightly distal distal to the medial length of the control handle 4.

Additional components of the control handle 4 are shown in greater detail in FIGS. 12-15 and assist with the understanding of its operation. As previously described, the top cover 24 and the bottom cover 26 are held together in part by the strain relief boot 34. Each half of a nose 36 extends from the distal end 8 of the top cover 24 and the bottom cover 26. A detent ring 38 extends as an annular protrusion about the nose 36. The detent ring 38 engages an interior wall of the strain relief boot 34 in order to secure the strain relief boot 34 to the top cover 24 and the bottom cover 26. A plurality of stakes 28 extends downward from the bottom side of the top cover 24. The stakes 28 are generally arranged adjacent to the perimeter of the top cover 24. A plurality of corresponding receptacles 30 is defined about the perimeter of the bottom cover 26. When the top cover 24 is mated with the bottom cover 26, each of the stakes 28 is inserted within a corresponding receptacle 30 on the bottom cover 26. The stakes 28 may friction fit within the receptacles 30 in order to aid in the attachment of the top cover 24 to the bottom cover 26. Additionally, each of the stakes 28 may be further secured within the corresponding receptacles 30, for example, by use of adhesives, ultrasonic welding, or other similar means.

A control coupling 40 protrudes proximally from the proximal cap 32. The control coupling 40 provides an interface between the control handle 4 and various pieces of equipment, for example, a radio frequency generator or a single processor. Although not depicted in FIGS. 12-15, a plurality of wires may travel through the catheter shaft 6 and extend through the control handle 4 for electrical connection with the control coupling 40. Exemplary wires may consist of electrode leads for either low power sensing or high power energy transfer.

As previously indicated, an actuator 12 is positioned between the top cover 24 and the bottom cover 26. As shown in FIG. 12, the actuator 12 defines a pivot aperture 13. The actuator 12 is pivotally attached via the pivot aperture 13 to the bottom cover 26. The pivot aperture 13 fits about an inner actuator post 42 extending upward from the bottom cover 26. A washer 48 may be inserted between the inner actuator post 42 and the actuator 12. An outer actuator post 44 extends through the pivot aperture 13 from the top side of the actuator 12 to interface coaxially with the inner actuator post 42. A washer 46 may be placed between the outer actuator post 44 and the top surface of the actuator 12. The outer actuator post 44 may further define a flange 45 about the top edge of its cylindrical body. The flange 45 extends to a greater diameter than the diameter of the pivot aperture 13, thus ensuring that the actuator 12 is retained about the outer actuator post 44. A set screw 50 extends axially through the outer actuator post 44 and is fastened to a corresponding receptacle within the center of the inner actuator post 42. Through this construction, the actuator 12 may pivot about the outer actuator post 44 while being restrained from vertical movement through its attachment to the bottom cover 26.

Figure 13:
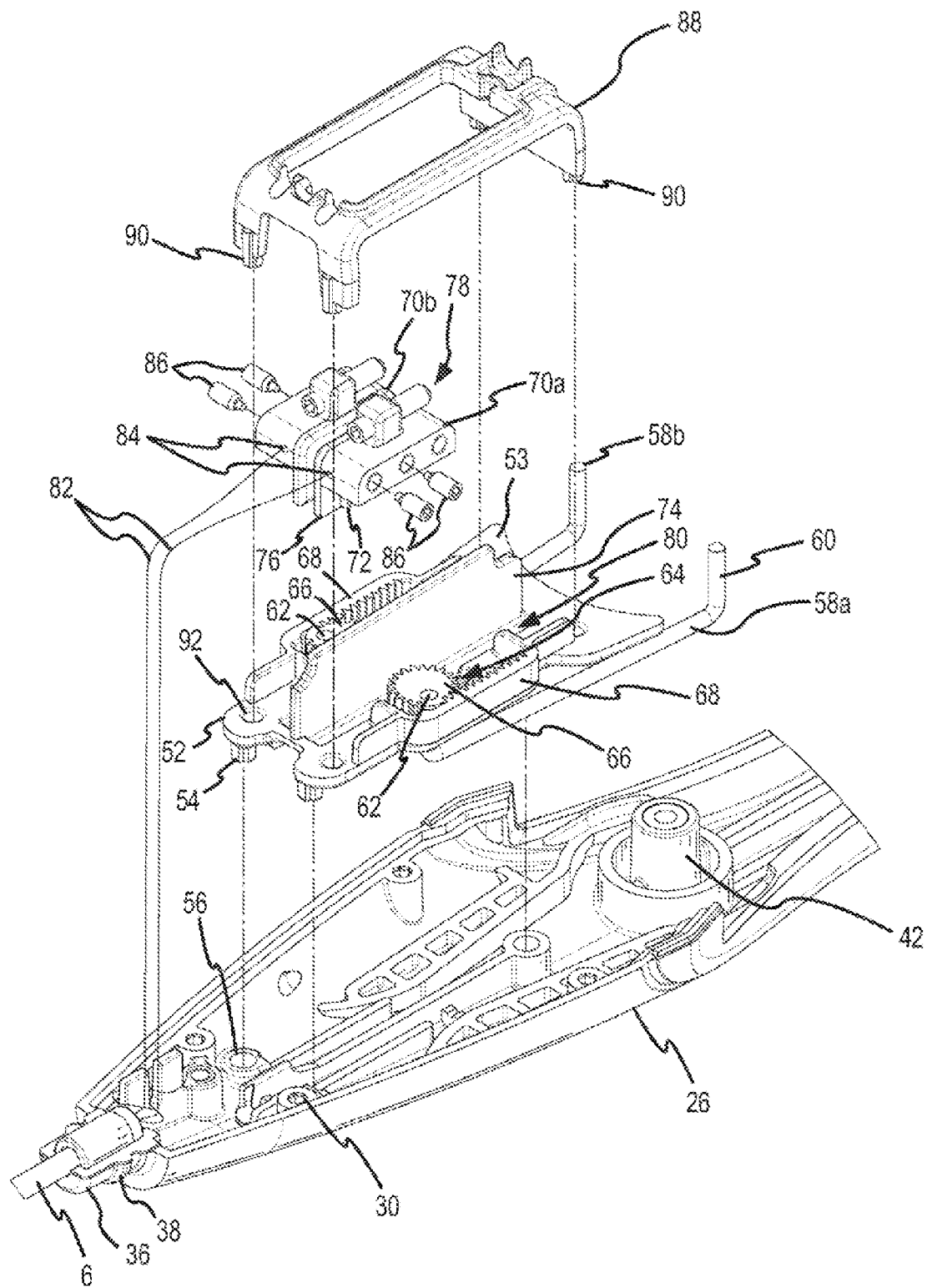
FIG. 13 is an exploded view of a portion of the control handle of the catheter assembly of FIG. 1.

As shown to good advantage in FIG. 13, a pair of deflection wires 82, which extend distally through the catheter shaft 6 to the distal tip 22 (see FIG. 3), extend proximally from the catheter shaft 6 into the control handle 4 where they connect with a tension mechanism 52. The tension mechanism 52 is linked to the actuator 12 via control arms 58, as further described herein, in order to exert tension independently on each of the deflection wires 82. By placing tension on the deflection wires 82, the ablation section 20 of the catheter shaft 6 can be caused to vary in its radius of curvature as further described below.

The tension mechanism 52 is composed of three primary components: a mechanism base 53, a sled manifold 78, and a mechanism cover 80. A plurality of stakes 90 protrude from the bottom edges of the mechanism cover 88. A plurality of corresponding receptacles 92 are formed within the mechanism base 53 for interfacing with the stakes 90 of the mechanism cover 88. By attaching the mechanism cover 88 to the mechanism base 53, the mechanism cover 88 retains the sleds 70a and 70b, within the tension mechanism 52. The mechanism base 53 similarly has a plurality of stakes 54 protruding from its bottom side. The stakes 54 are aligned to interface with a plurality of receptacles 56 defined within the bottom cover 26 of the control handle 4. By inserting the stakes 54 into the receptacles 56 on the mechanism base 53, the tension mechanism 52 is secured within the control handle 4 to bottom cover 26.

The sled manifold 78 is composed of two symmetrical sleds 70a, 70b. The deflection wires 82 terminate within a respective deflection wire receptacle 84 on the distal end of each of the sleds 70a, 70b. The deflection wires 82 are fastened within the sleds 70a, 70b by one or more set screws 86 that are threaded into apertures in each of the lateral sides of the sleds 70a, 70b to impinge the deflection wires 82 in the deflection wire receptacles 84, thereby fastening the deflection wires 82 to the sled manifold 78. Each sled 70a, 70b also defines a sidewall 76 on the interior sides of each of the sled manifolds 78. Thus, the sidewalls 76 of each of the sleds 70a, 70b face each other. The sidewalls 76 further extend below the bottom of the sled manifolds 78. A series of teeth forming a sled rack 72 protrudes from each of the outside faces of the sled sidewalls 76 underneath the sled manifolds 78.

A sled separator 74 protrudes from the mechanism base 53 as a longitudinally oriented wall positioned medially on the mechanism base 53. On each side of the sled separator 74, a stationary rack 68 is supported on the mechanism base 53. Each stationary rack 68 is formed as a low three-sided wall with a longer longitudinal portion and two shorter portions oriented orthogonal to the longer portion at each of its proximal and distal ends and which extends toward the sled separator 74. A series of teeth are formed along the interior sides of each of the longitudinal walls of the stationary racks 68. A pinion gear 66 is positioned between the stationary rack 68 and the sled separator 74 and is designed to interface with the teeth of the stationary rack 68.

Figure 14:
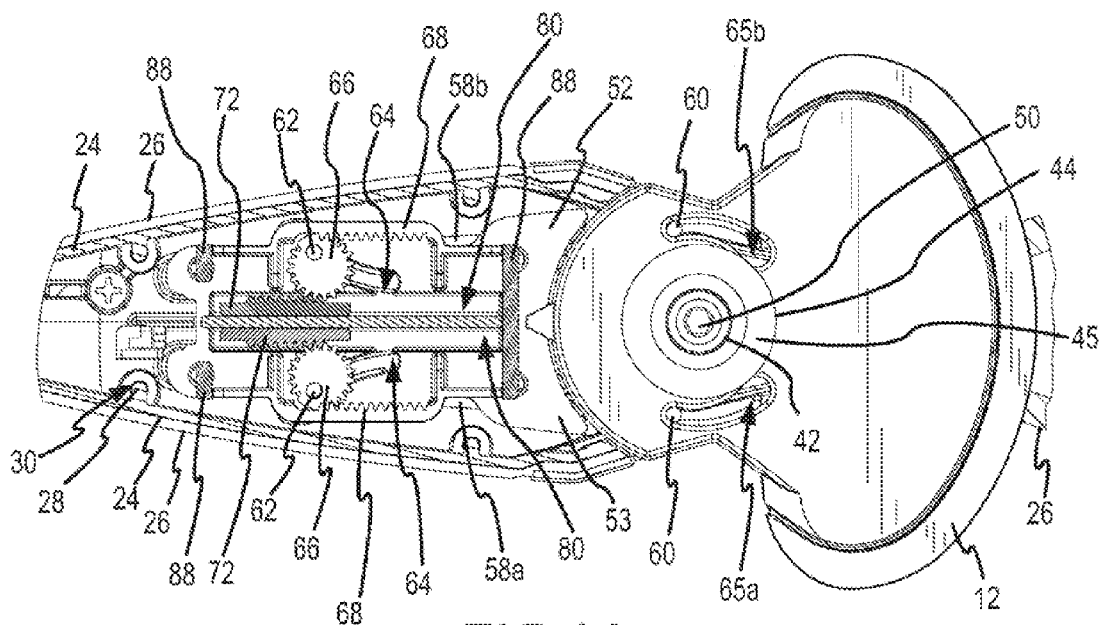
FIG. 14 is a cross-section view of the control handle of the catheter assembly of FIG. 1 taken along line 14-14 as indicated in FIG. 1.

As shown to good advantage in FIG. 14, when the tension mechanism 52 is fully assembled, each of the sleds 70a, 70b is positioned on opposing sides of the sled separator 74 with the sidewalls 76 of the sleds 70a and 70b facing opposing sides of the sled separator 74. Each of the sled racks 72 additionally interfaces with a corresponding pinion gear 66 on each side of the sled separator 74.

A sled recess 80 is formed within the mechanism base 53 on each side of the sled separator 74 and extends along the length of the sled separator 74. Each of the sled recesses 80 is designed to accept a bottom edge of the sidewall 76 of each of the sleds 70a, 70b, which extend below the teeth of the sled rack 72. The sidewalls 76 of each of the sleds 70a and 70b are thus confined to travel linearly within the sled recess 80 along each side of the sled separator 74.

As previously stated, the tension mechanism 52 is connected with the actuator 12 by a pair of control arms 58a, 58b. Each of the control arms 58a, 58b is composed of a long shaft that bends upward at a proximal end 10 to form a proximal post 60 and then bends upward at a distal end 8 to form a distal post 62. As shown to good advantage in FIGS. 14 and 15, the mechanism base 53 defines a pair of arcuate control arm slots 64 on opposing sides of the sled separate 74. Additionally, the pinion gear 66 defines an aperture for acceptance of the distal post 62. Each control arm 58a, 58b is thereby connected to a respective pinion gear 66 by inserting the distal post 62 through a respective control arm slot 64 to interface with the aperture in the pinion gear, which is positioned above the control arm slot 64.

Figure 15:
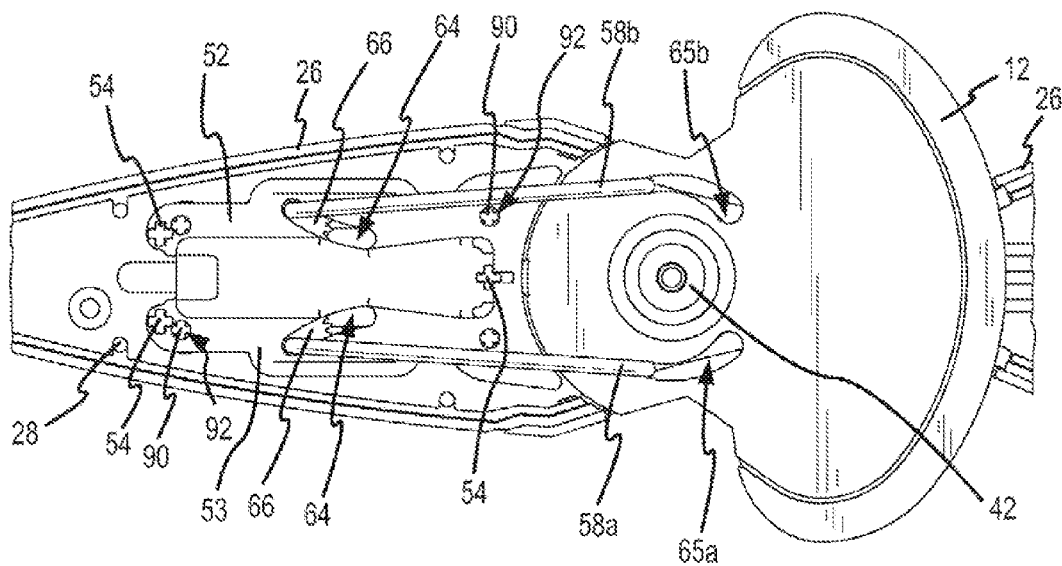
FIG. 15 is a bottom plane view of the control handle of the catheter assembly of FIG. 1 with the bottom cover removed.

As shown in FIGS. 14 and 15, the actuator 12 defines a pair of arcuate actuator slots 65a, 65b positioned laterally on opposing sides of the pivot aperture 13. The actuator slots 65a, 65b are designed to accept the proximal posts 60 of each of the control arms 58. The proximal posts 60 extend upward through a corresponding actuator slot 65a, 65b connection between the actuator 12 and the tension mechanism 52. As shown in FIGS. 14 and 15, when the actuator 12 is in a rest or equilibrium position, i.e., the actuator 12 is not deflected laterally with respect to the longitudinal orientation of the control handle 4, and the proximal posts 60 are positioned adjacent the distal ends of each of the actuator slots 65a, 65b.

Figure 16A:
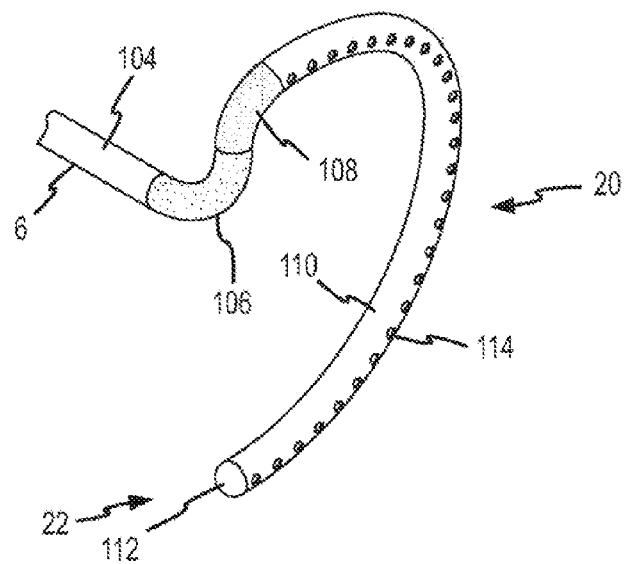
FIG. 16A is an isometric view of the distal end of the catheter in a first actuation status correlative to the actuation status of the control handle as depicted in FIG. 16B.
Figure 16B:
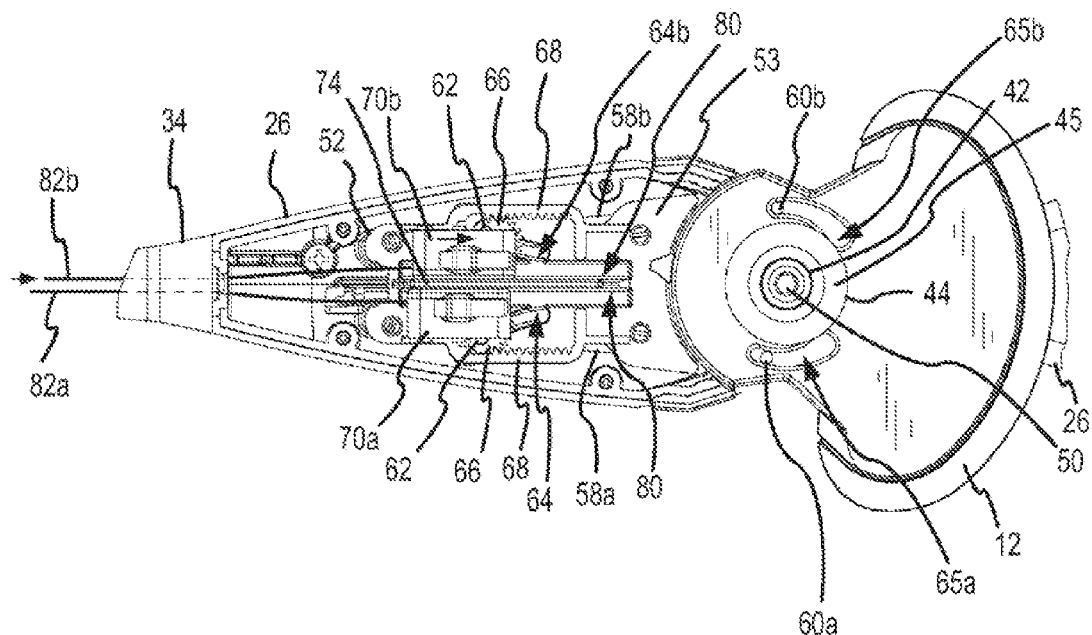
FIG. 16B is top plan view of the control handle of the catheter assembly of FIG. 1 with the top cover and mechanism cover removed, and shown in a first actuation status correlative to the actuation status of the catheter as depicted in FIG. 16A.

The operation of the tension mechanism 52 when the actuator 12 is pivoted is best understood in conjunction with FIGS. 14, 15, 16B, 17B, and 18B. In an equilibrium position, each of the proximal posts 60 of the control arms 58a, 58b resides within a respective actuator slot 65a, 65b adjacent the distal ends of the actuator slots 65a, 65b. The pinion gears 66 are similarly positioned at the distal end of the stationary racks 68. Further, the sleds 70a, 70b are positioned generally distal to the pinion gears 66. The pinion gears 66 interface with the teeth of both the stationary racks 68 and the sled racks 72 on each of the sleds 70a, 70b. When the actuator 12 is deflected slightly in one direction, for example, laterally to the left as shown in FIG. 16B, the proximal post 60b within the right actuator slot 65b interfaces with and is pulled by the distal end of the right actuator slot 65b. However, the proximal post 60a within the left actuator slot 65b remains stationary as the left actuator slot 65a slides past the respective post 60. The force on the actuator post 60b in the right actuator slot 65b pulls the right control arm 58b proximally and thus pulls the distal post 62 within the right control arm slot 64b proximally. As the pinion gear 66 on the right side is linked with the distal post 62, the pinion gear 66 begins to rotate counterclockwise and moves proximally along the stationary rack 68. The pinion gear 66 similarly engages the sled rack 72 on the right sled 70b and pulls the right sled 70b proximally. As the right deflection wire 82b is attached to the right sled 70b, the right deflection wire 82b is pulled proximally and the distal end of the catheter 6 will be deflected accordingly in a first direction. It should be apparent that movement of the actuator 12 to the lateral right would similarly translate through the tension mechanism 52 to place tension on the left pull wire 82a and deflect the distal end of the catheter 6 in a second direction substantially opposite the first direction.

Figure 17A:
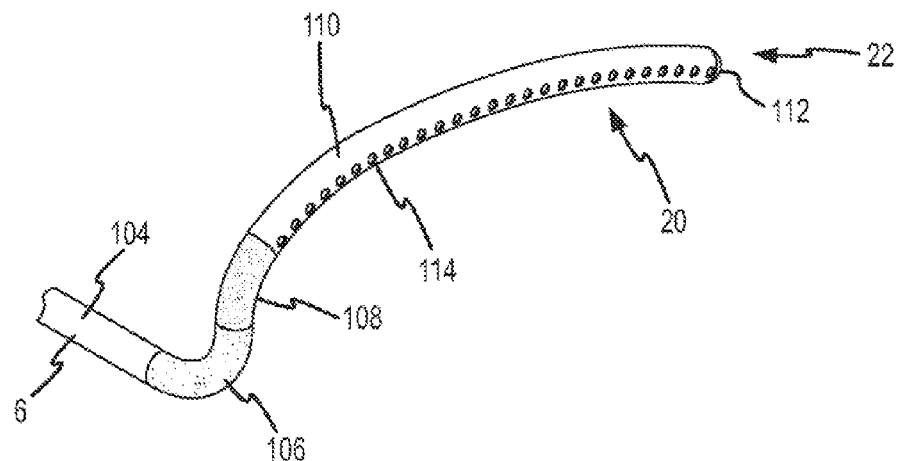
FIG. 17A is an isometric view of the distal end of the catheter of FIG. 1 in a second actuation status correlative to the actuation status of the control handle as depicted in FIG. 17B.
Figure 17B:
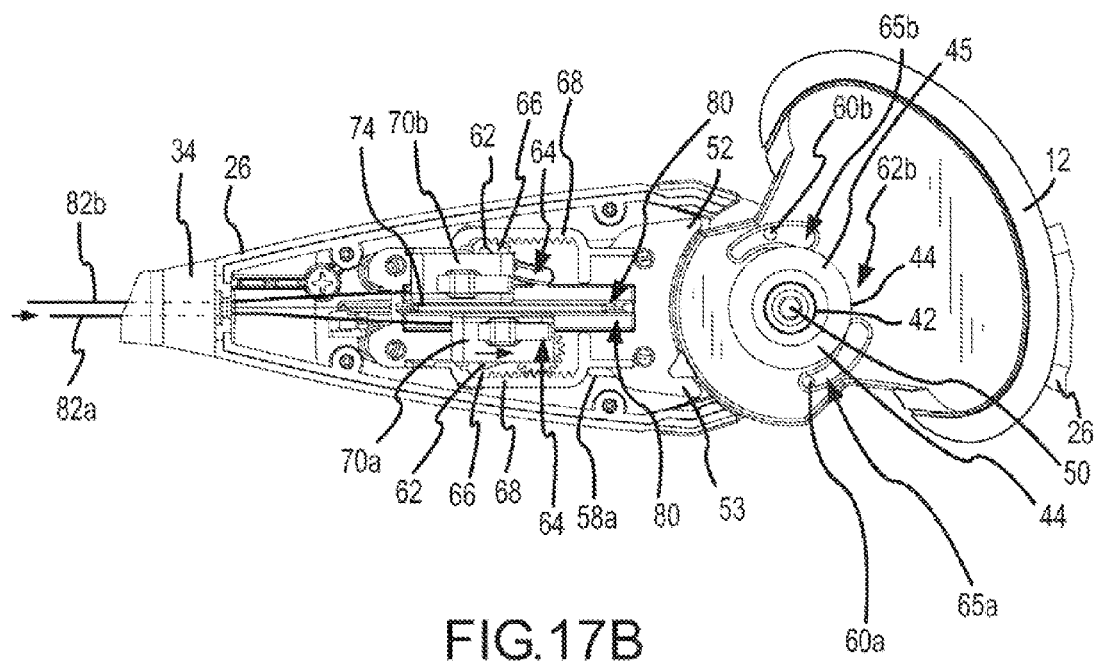
FIG. 17B is top plan view of the control handle of the catheter assembly of FIG. 1 with the top cover and mechanism cover removed, in a second actuation status correlative to the actuation status of the catheter as depicted in FIG. 17A.
Figure 18A:
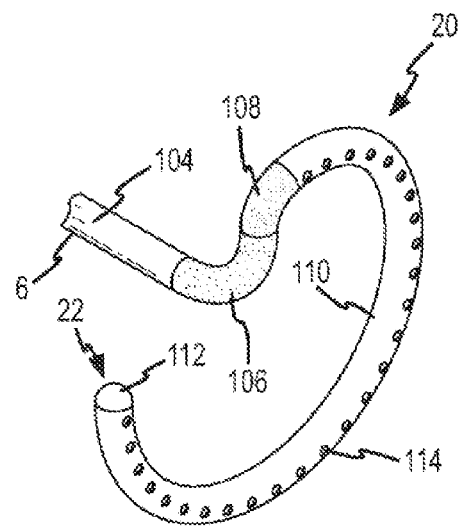
FIG. 18A is an isometric view of the distal end of the catheter of FIG. 1 in a third actuation status correlative to the actuation status of the control handle as depicted in FIG. 18B.
Figure 18B:
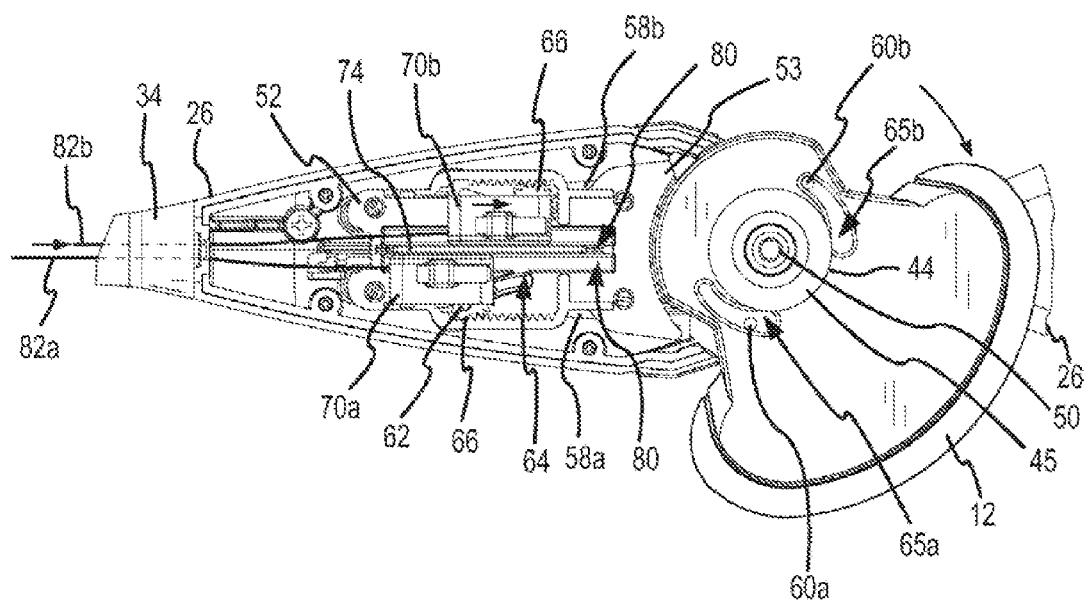
FIG. 18B is top plan view of the control handle of the catheter assembly of FIG. 1 with the top cover and mechanism cover removed, in a third actuation status correlative to the actuation status of the catheter as depicted in FIG. 18A.

FIGS. 16A-18B depict the effect of the actuator 12 on the distal end of a catheter 6 of a first exemplary configuration. As shown in FIG. 16A, the catheter 6 is performed in a semicircular or C-shape. As indicated in FIG. 16B, this C-shape is the static or equilibrium shape of the ablation section 20 of the catheter 6 as the actuator 12 is only slightly deflected laterally left. FIG. 17B depicts the actuator 12 deflected significantly laterally to the right. In this position, the left sled 70a moves substantially proximally and the left deflection wire 82a is pulled in the proximal direction to increase the tension thereon. Note the proximal post 60b within the right actuator slot 65b is stationary, the right sled 70b remains in a proximal position, and no tension is placed on the right deflection wire 82b. The corresponding effect on the distal end of the catheter 6 is shown in FIG. 17A, wherein the third curved section 110 is substantially straightened from the original C-shape. Alternately, when the actuator 12 is substantially deflected to the lateral left, as shown in FIG. 18B, the right sled 70b moves substantially proximally and the right deflection wire 82b is pulled in the proximal direction to increase the tension thereon. Note the proximal post 60a within the left actuator slot 65a is stationary, the left sled 70a remains in a proximal position, and no tension is placed on the left deflection wire 82a. The corresponding effect on the distal end of the catheter 6 is shown in FIG. 18A, wherein the third curved section 110 is pulled into a substantially tighter curve with a smaller radius than the original C-shape.

Figure 19A:
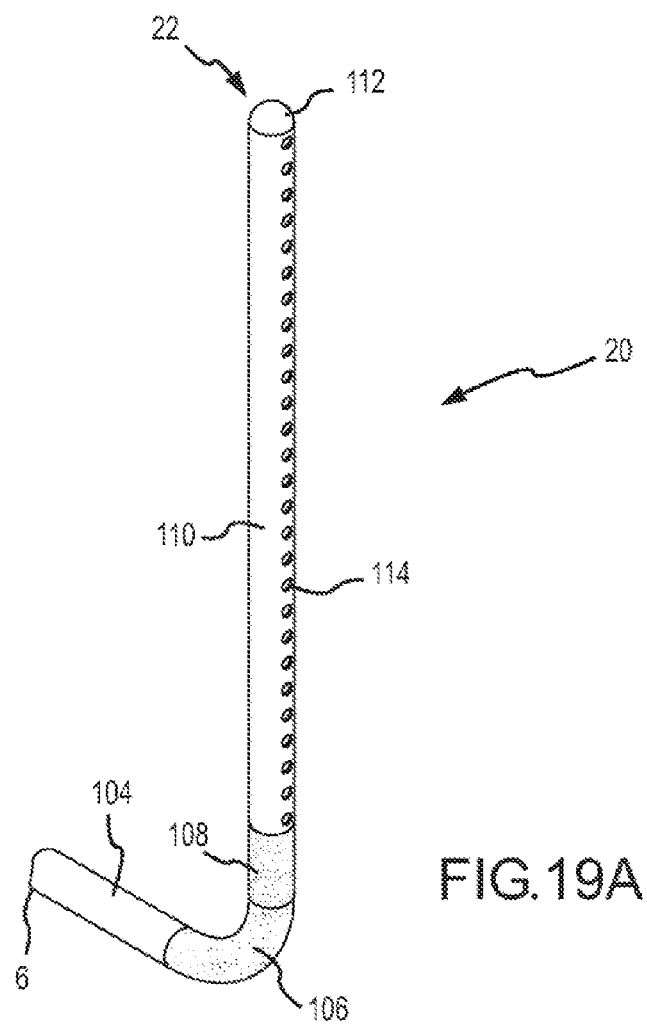
FIG. 19A is an isometric view of the distal end of an alternate embodiment of a catheter according to the present invention in a first actuation status correlative to the actuation status of the control handle as depicted in FIG. 19B.
Figure 19B:
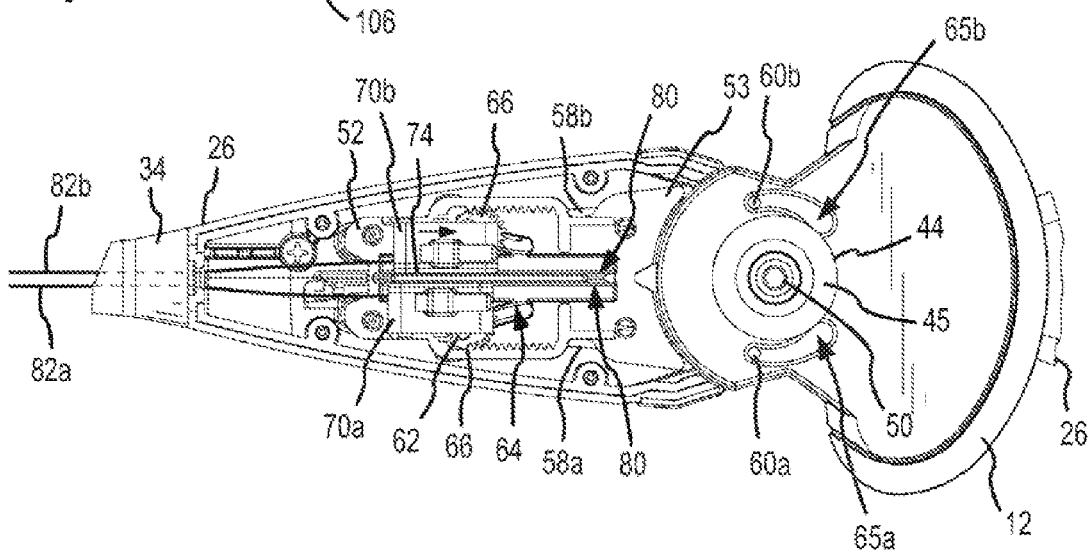
FIG. 19B is top plan view of the control handle of the type used in the catheter assembly of FIG. 1 with the top cover and mechanism cover removed, in a first actuation status correlative to the actuation status of the catheter as depicted in FIG. 19A.
Figure 20A:
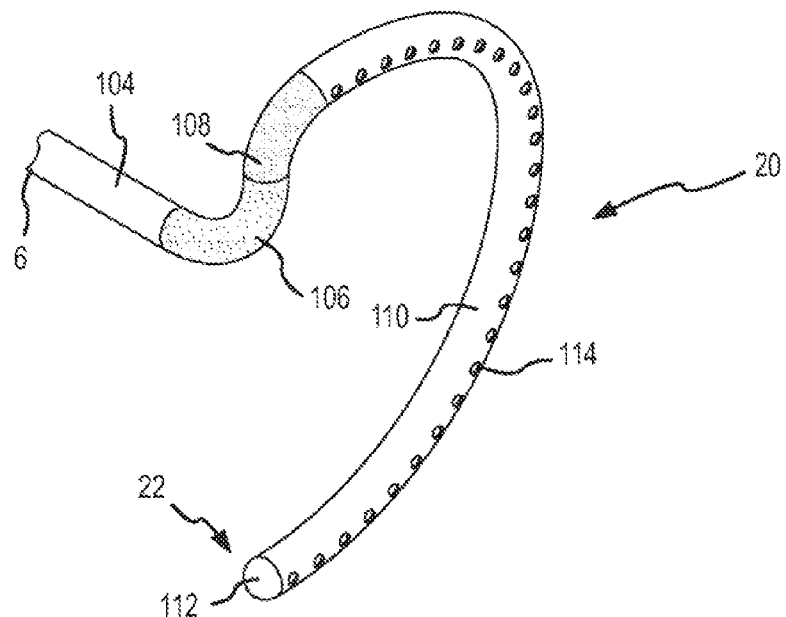
FIG. 20A is an isometric view of the distal end of the catheter of FIG. 19A in a second actuation status correlative to the actuation status of the control handle as depicted in FIG. 20B.
Figure 20B:
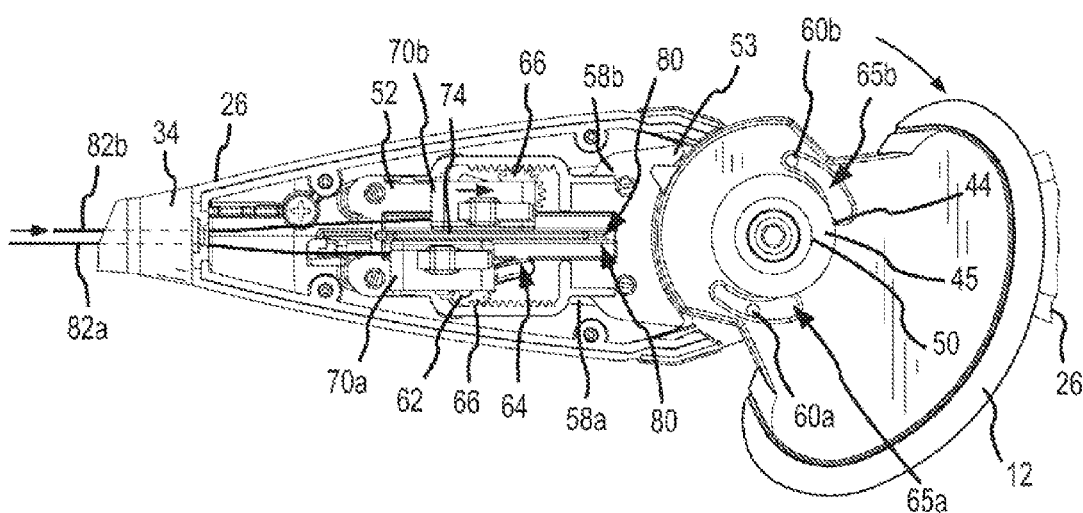
FIG. 20B is top plan view of the control handle of the type used in the catheter assembly of FIG. 1 with the top cover and mechanism cover removed, in a second actuation status correlative to the actuation status of the catheter as depicted in FIG. 20A.
Figure 21A:
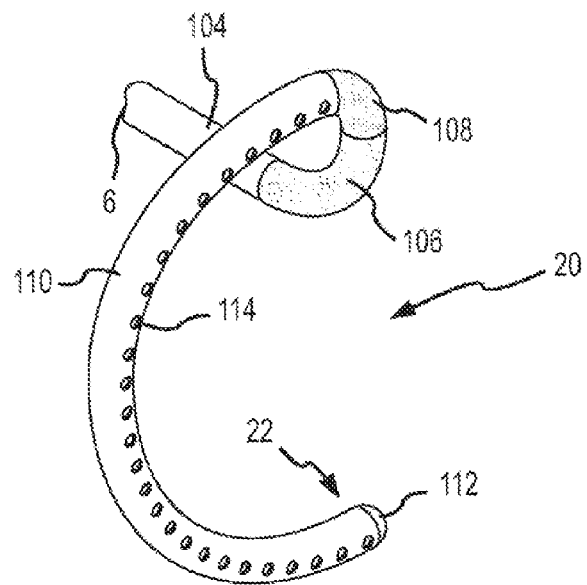
FIG. 21A is an isometric view of the distal end of the catheter of FIG. 19A in a third actuation status correlative to the actuation status of the control handle as depicted in FIG. 21B.
Figure 21B:
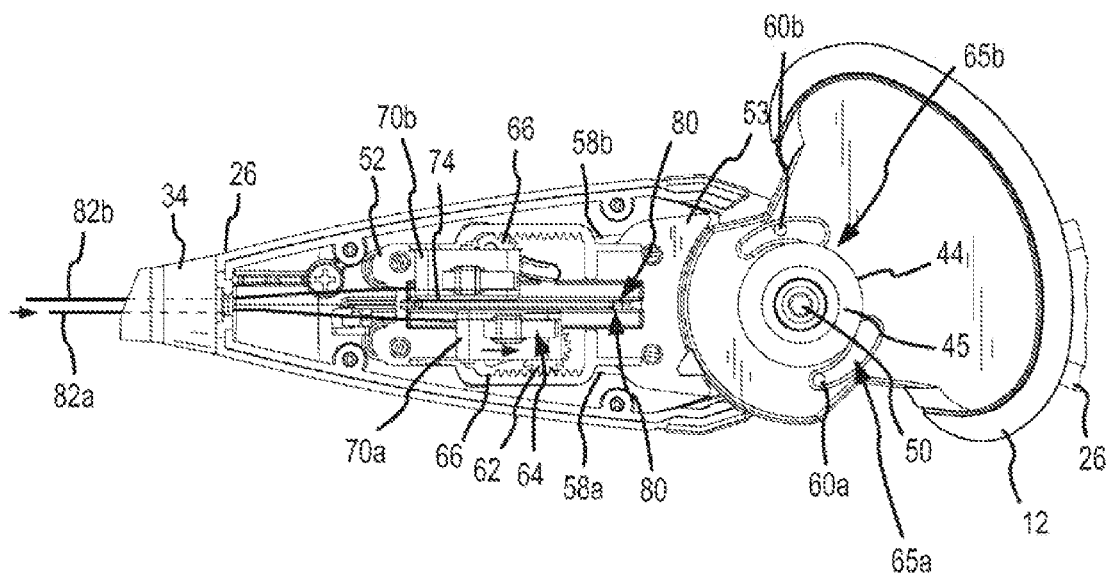
FIG. 21B is top plan view of the control handle of the type used in the catheter assembly of FIG. 1 with the top cover and mechanism cover removed, in a third actuation status correlative to the actuation status of the catheter as depicted in FIG. 21A.

FIGS. 19A-21B depict the effect of the actuator 12 on the distal end of a catheter 6 of a second exemplary configuration. As shown in FIG. 19A, the catheter 6 is performed in a substantially straight, linear shape. As indicated in FIG. 16B, this linear shape is the static or equilibrium shape of the ablation section 20 of the catheter 6 as the actuator 12 is not deflected in either direction. FIG. 20B depicts the actuator 12 deflected significantly laterally to the left. In this position, the right sled 70b moves substantially proximally and the right deflection wire 82b is pulled in the proximal direction to increase the tension thereon. Note the proximal post 60a within the left actuator slot 65a is stationary, the left sled 70a remains in a proximal position, and no tension is placed on the left deflection wire 82a. The corresponding effect on the distal end of the catheter 6 is shown in FIG. 20A, wherein the ablation section 20 is pulled into a clockwise curve when viewed from the distal end. Alternately, when the actuator 12 is substantially deflected to the lateral right, as shown in FIG. 21B, the left sled 70a moves substantially proximally and the left deflection wire 82a is pulled in the proximal direction to increase the tension thereon. Note the proximal post 60b within the right actuator slot 65b is stationary, the right sled 70b remains in a proximal position, and no tension is placed on the right deflection wire 82b. The corresponding effect on the distal end of the catheter 6 is shown in FIG. 21A, wherein the ablation section 20 is pulled into a counterclockwise curve when viewed from the distal end.

Figure 22:
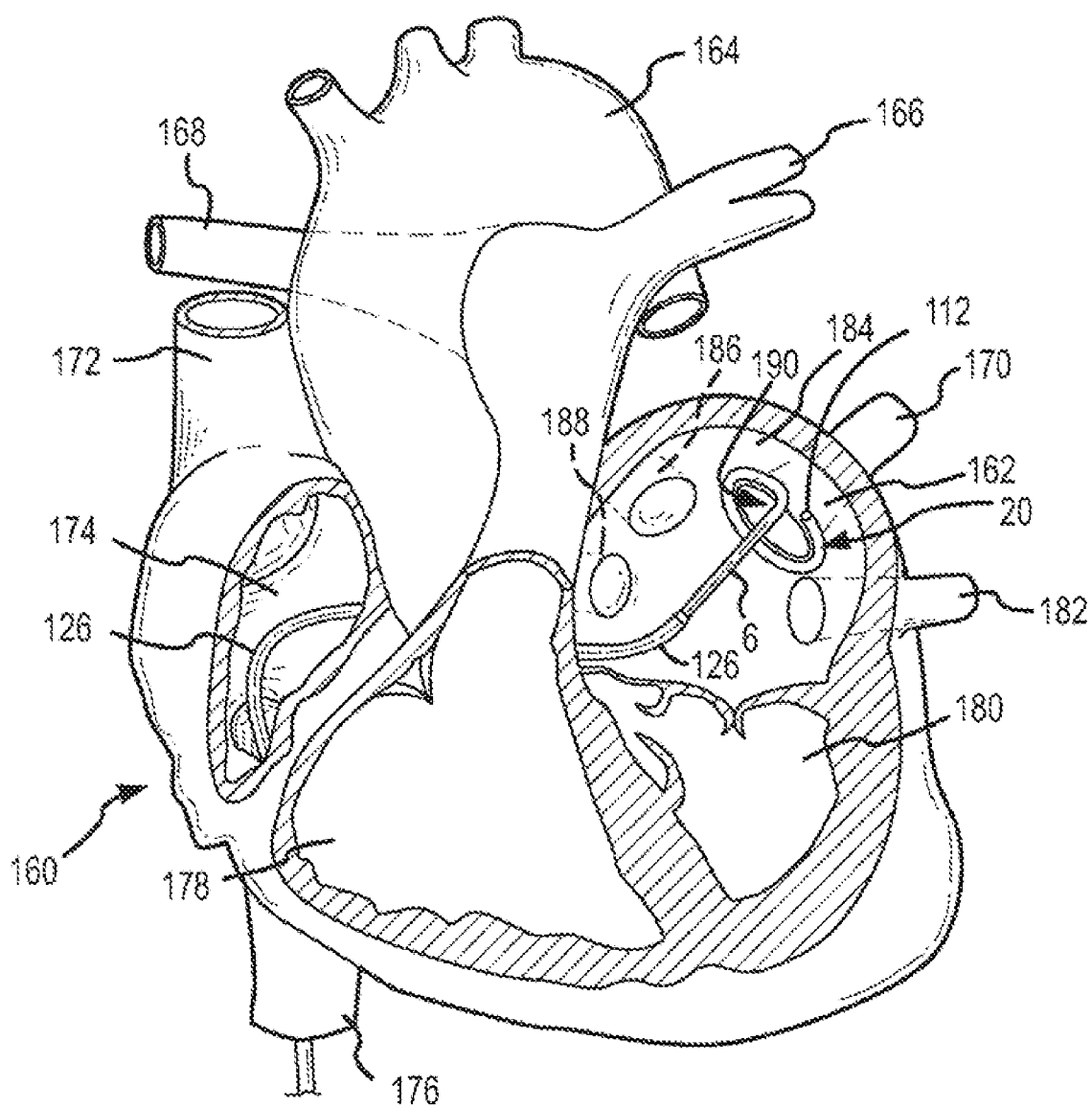
FIG. 22 is an isometric view of a heart with portions of the atria and ventricles cut-away to reveal positioning of a generic version of the catheter of the present invention in the left atrium, adjacent to the left superior pulmonary vein performing a linear ablation.

FIG. 22 schematically depicts the catheter 6 and ablation electrode section 20 according to a generic embodiment of the present invention being used to ablate tissue about a left superior pulmonary vein 170. FIG. 22 includes a number of primary components of the heart 160 to orient the reader. In particular, starting in the upper left-hand portion of FIG. 22, and working around the periphery of the heart 160 in a counterclockwise fashion, the following parts of the heart 160 are depicted: the superior vena cava 172, the right atrium 174, the inferior vena cava 176, the right ventricle 178, the left ventricle 180, the left inferior pulmonary vein 182, left superior pulmonary vein 170, the left atrium 184, the right superior pulmonary vein 186, the right inferior pulmonary vein 188, the left pulmonary artery 166, the arch of the aorta 164, and the right pulmonary artery 168.

The distal end of the ablation electrode section 20 is positioned adjacent to the ostium 190 of the left superior pulmonary vein 170 using known procedures. For example, to place the ablation electrode section 20 in the position shown in FIG. 22, the right venous system may be first accessed using the "Seldinger technique." In this technique, a peripheral vein (such as a femoral vein) is first punctured with a needle and the puncture wound is dilated with a dilator to a size sufficient to accommodate an outer guiding portion of introducer fluidly. The outer guiding portion of introducer fluidly with at least one hemostatic valve is seated within the dilated puncture wound while maintaining relative hemostasis. From there, the outer guiding portion of introducer fluidly is advanced along the peripheral vein, into the inferior vena cava 176, and into the right atrium 174. A transeptal sheath may be further advanced through the outer guiding introducer 26 to create a hole in the interatrial septum between the right atrium 174 and the left atrium 184.

Once the outer guiding portion of introducer fluidly is in place in the right atrium 174, an inner guiding portion of introducer 126, housing the catheter 6 with the ablation electrode section 20 on the distal end, is introduced through the hemostatic valve of the outer guiding portion of introducer fluidly and navigated into the right atrium 174, through the hole in the interatrial septum, and into the left atrium 184. Once the inner guiding portion of introducer 126 is in the left atrium 184, the ablation electrode section 20 of the catheter 6 and may be advanced through the distal tip of the inner guiding portion of introducer 126. The form of the catheter 6 may be chosen in advance by the clinician to account for the particular procedure to be performed or the particular size of the chamber in which the procedure is to be performed. For example, catheters with different sized base radii of the distal ablation section may be available to account for a patient's particular physiology. The ablation electrode section 20, as shown in FIG. 22, is placed the ostium 190 of the left superior pulmonary vein 170 to contact the tissue of the myocardium around the vein. By forming the distal end of the catheter 6 in a spiral-like curve by material selection, molding, and wire tension as described above, the ablation electrode section 20 can be oriented transverse to the straight section of the catheter 6 for placement about the ostium 190. The configuration of the ablation electrode section 20 may be further manipulated using the control handle to vary the length of and radius of the curve to best fit about the ostium 190 and to ensure consistent contact with the myocardial tissue. Other configuration of the ablation electrode section 20 may be used to greater advantage on tissue surfaces of other shapes.

In an exemplary embodiment based upon the catheter configuration of FIGS. 16A, 17A, and 18A, the ablation electrode section 20 extends from or as part of the third curved section and is thus oriented in a plane transverse to the orientation of the straight section of the catheter 6. Because the third curved section is curved at rest, the ablation electrode section 20 forms a loose curve that may be desirable for ablation of tissue about the ostium of a larger diameter vessel. When a first deflection wire is tensioned, for example, as indicated in FIG. 17B, the distal end 8 of the catheter shaft 6 flattens the curve as depicted in FIG. 17A. This orientation allows a clinician to easily position and use the tip electrode 112 to perform spot ablation. When the second deflection wire is tensioned, for example, as indicated in FIG. 18B, the distal end 8 of the catheter shaft 6 forms a small, tight curve as depicted in FIG. 18A. The creation of such a small curve may be desirable for ablation the tissue about the ostium of a small diameter vessel.

While the ablation electrode 20 is placed about the left superior pulmonary vein 170, the ablation electrode section 20 may be energized to create the desired lesion about the left superior pulmonary vein 170. The RF energy emanating from the ablation electrode section 20 is transmitted through the conductive fluid medium, which flows through the fluid lumen, through the porthole openings, and impacts the adjacent tissue. Thus, a lesion is formed in the tissue by the RF energy. The RF energy is conducted into the adjacent tissue and the heated conductive fluid convectively affects the temperature of the tissue. In order to form a sufficient lesion, it is desirable to raise the temperature of the tissue to at least 50° C. for an appropriate length of time (e.g., one minute). Thus, sufficient RF energy must be supplied to the electrode to produce this lesion-forming temperature in the adjacent tissue for the desired duration.

Figure 23:
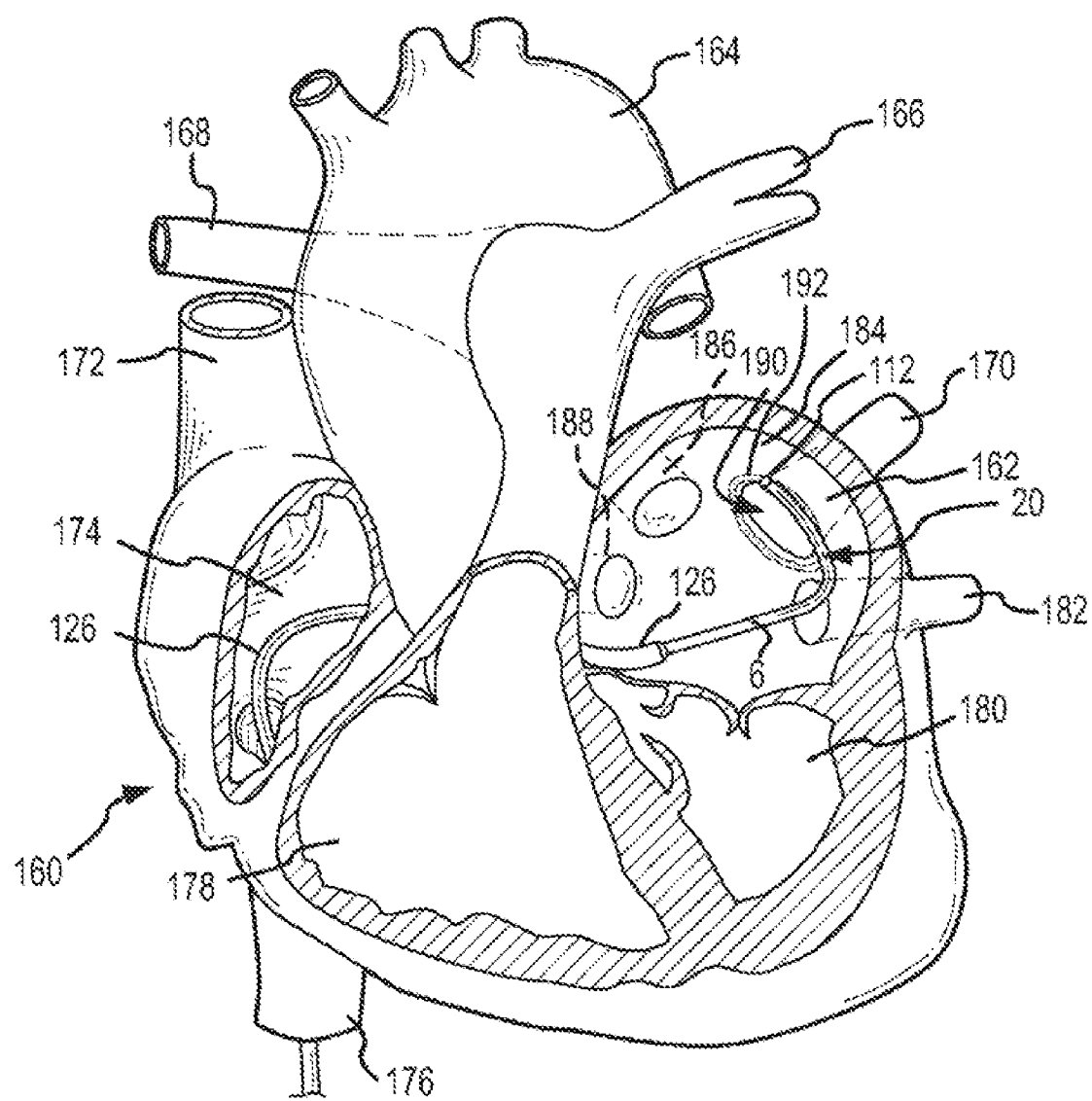
FIG. 23 is an isometric view of a heart with portions of the atria and ventricles cut-away to reveal positioning of a generic version of the catheter of the present invention in the left atrium, adjacent to the left superior pulmonary vein performing a touch-up ablation using the tip electrode.

Should spot ablation additionally be desired, the distal end of the catheter may be manipulated to appropriately place the tip electrode adjacent the target cardiac tissue as shown in FIG. 23. For example, the virtual electrode section may create a circular linear lesion 192 about the ostium 190 of the left superior pulmonary vein 170. However, there may be a small gap in the lesion as the ablation electrode section 20 may be unable to be formed into a complete circle. In this instance, it is a simple procedure to manipulate the distal tip of the catheter 6 to the location of the gap and ablate the tissue to complete a continuous lesion using the tip electrode 112. The deflection wires may be used to adjust the radius of the ablation section 2 of the catheter 6 to flatten the curve and position the tip electrode 112 against the myocardial tissue to complete the lesion 192.

The benefits of the combination of a variable radius catheter with a linear lesion creating virtual electrode and a standard electrode tip are several. First, the virtual electrode design results in the creation of consistent higher quality linear lesions than other types of ablation electrode designs or methods of use. Second, the variability of the radius of the distal end of the catheter allows for placement of the ablation electrode section adjacent many different surface contours of tissue as well as for creating lesions adjacent to or within various ostium, for example, treatment of the pulmonary vein interfaces within the left atrium. Third, the tip electrode allows the clinician to quickly and easily apply ablation energy to a particular spot location. For example, in the event that the virtual electrode failed to complete a continuous linear lesion, the tip electrode can be used for spot ablation of the area of discontinuity without having to remove a separate linear lesion forming catheter and insert a new catheter for performing a specialized tip ablation function. Further, because the distal end of the catheter is manipulable by the control handle, the tip electrode can be appropriately oriented to reach almost any desired position for ablation of tissue.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. A catheter assembly comprising:
   a control handle at a proximal end of the catheter assembly;
   a catheter shaft attached to the control handle and extending distally therefrom;
   a virtual electrode structure provided within a distal end section of the catheter shaft;
   a fluid lumen defined within the catheter shaft extending distally into the distal end section, wherein the fluid lumen is in fluid communication with the virtual electrode structure; and
   at least one control mechanism interconnected between the distal end section of the catheter and the control handle, the at least one control mechanism including an actuator;
   wherein upon actuation of the at least one control mechanism at the control handle, at least a portion of the distal end section of the catheter shaft is caused to form a curved section, the actuator deflecting to move a first sled and pull a first deflection wire thereon while a second sled remains stationary, wherein the first sled is operatively coupled to the actuator by a toothed rack and a pinion gear, and
   wherein upon further manipulation of the at least one control mechanism, the radius of the curved section is variable.

2. The catheter assembly of claim 1, further comprising a tip electrode joined to a distal tip of the catheter shaft.

3. The catheter assembly of claim 2, wherein the virtual electrode structure is positioned adjacent and proximal to the tip electrode.

4. The catheter assembly of claim 1, wherein the virtual electrode structure further comprises
   an array of apertures defined within an exterior wall of the catheter shaft, wherein the apertures penetrate the exterior wall to fluidly interface with the fluid lumen; and
   a first electrode lead positioned within the distal end section of the catheter shaft such that at least a portion of the first electrode lead is exposed to the interior of the fluid lumen.

5. The catheter assembly of claim 4, further comprising a tip electrode joined to a distal tip of the catheter shaft, wherein the first electrode lead is further electrically coupled with the tip electrode.

6. The catheter assembly of claim 4 further comprising a second electrode lead housed within the catheter shaft and electrically coupled with a tip electrode joined to a distal tip of the catheter shaft.

7. The virtual electrode catheter system of claim 6, wherein the second electrode lead comprises the second deflection wire.

8. The catheter assembly of claim 1, wherein at least a portion of the distal end section of the catheter shaft is oriented in a plane transverse to a longitudinal orientation of the catheter shaft proximal to the distal end section.

9. The catheter assembly of claim 8, wherein the at least one control mechanism further comprises
   a first control mechanism for decreasing the radius of the curved section; and
   a second control mechanism for increasing the radius of the curved section.

10. The catheter assembly of claim 9, further comprising a tip electrode joined to a distal tip of the catheter shaft, wherein
    the first deflection wire is housed within the catheter shaft, attached at its proximal end to an actuator in the control handle, and anchored at its distal end within the catheter shaft at a first position proximal and adjacent to the tip electrode; and
    the second control mechanism further comprises a second deflection wire housed within the catheter shaft, attached at its proximal end to the actuator in the control handle, and anchored at its distal end within the catheter shaft at a second position proximal and adjacent to the tip electrode.

11. The catheter assembly of claim 10, wherein the first position of the first deflection wire is spaced 180 degrees apart from the second position of the second deflection wire.

12. The catheter assembly of claim 10, wherein the actuator is adapted to place the at least one of the first deflection wire and the second deflection wire under variable degrees of tension.

13. The catheter assembly of claim 8, wherein the at least one control mechanism further comprises
    a first control mechanism that imparts a clockwise curve to the curved section; and
    a second control mechanism that imparts a counterclockwise curve to the curved section.

14. The catheter assembly of claim 13, further comprising a tip electrode joined to a distal tip of the catheter shaft, wherein
    the first deflection wire is housed within the catheter shaft, attached at its proximal end to an actuator in the control handle, and anchored at its distal end within the catheter shaft at a first position proximal and adjacent to the tip electrode; and
    the second control mechanism further comprises a second deflection wire housed within the catheter shaft, attached at its proximal end to the actuator in the control handle, and anchored at its distal end within the catheter shaft at a second position proximal and adjacent to the tip electrode.

15. The catheter assembly of claim 13, wherein the first position of the first deflection wire is spaced 180 degrees apart from the second position of the second deflection wire.

16. The catheter assembly of claim 13, wherein the actuator is adapted to place the at least one of the first deflection wire and the second deflection wire under variable degrees of tension.

17. A virtual electrode catheter system comprising:
- a control handle at a proximal end of the catheter system, the control handle further comprising an actuator mechanism;
- a catheter shaft attached to the control handle and extending distally therefrom, wherein at least a portion of a distal end section of the catheter shaft is oriented in a plane transverse to a longitudinal orientation of the catheter shaft proximal to the distal end section;
- a tip electrode joined to a distal tip of the catheter shaft,
- an array of apertures defined within an exterior wall of the distal end section of the catheter shaft;
- a fluid lumen defined within the catheter shaft extending distally into the distal end section of the catheter shaft, wherein the fluid lumen is at least partially bounded within the distal end section by the exterior catheter wall, and
  - wherein the apertures in the exterior wall fluidly interface with the fluid lumen;
- a first electrode lead coupled at a proximal end with the control handle and positioned at a distal end within the distal end section of the catheter shaft such that at least a portion of the first electrode lead is exposed to the interior of the fluid lumen;
- a first deflection wire housed within the catheter shaft, connected at its proximal end with the actuator mechanism in the control handle, and anchored at its distal end within the catheter shaft at a first position proximal and adjacent to the tip electrode, the first deflection wire operatively associated with a first sled, wherein the first sled is operatively coupled to the actuator mechanism by a first toothed rack and a first pinion gear; and
- a second deflection wire housed within the catheter shaft, connected at its proximal end with the actuator mechanism in the control handle, and anchored at its distal end within the catheter shaft at a second position proximal and adjacent to the tip electrode, the first deflection wire operatively associated with a second sled;
- wherein moving the control handle in a first direction moves the first sled to pull the first deflection wire and increase tension on the first deflection wire while the second sled remains stationary; and
- wherein moving the control handle in a second direction moves the second sled to pull the second deflection wire while the first sled remains stationary.

18. The virtual electrode catheter system of claim 17, wherein the array of apertures are positioned adjacent and proximal to the tip electrode.

19. The virtual electrode catheter system of claim 17, further comprising a second electrode lead housed within the catheter shaft, coupled at a proximal end with the control handle, and coupled at a distal end to the tip electrode.

20. The virtual electrode catheter system of claim 19, wherein the second electrode lead comprises the second deflection wire.

21. The virtual electrode catheter system of claim 17, wherein upon actuation of the actuator mechanism at the control handle, at least a portion of the distal end section of the catheter shaft is caused to form a curved section.

22. The virtual electrode catheter system of claim 21, wherein upon manipulation of the actuator mechanism the radius of the curved section is variable.

23. The virtual electrode catheter system of claim 17, wherein
- the actuator mechanism is adapted to place the first deflection wire under variable degrees of tension that imparts a clockwise curve to the distal end section; and
- the actuator mechanism is adapted to place the second deflection wire under variable degrees of tension that imparts a counterclockwise curve to the distal end section.

24. The virtual electrode catheter system of claim 17, wherein
- the actuator mechanism is adapted to place the first deflection wire under variable degrees of tension that decreases a radius of curvature of the distal end section; and
- the actuator mechanism is adapted to place the second deflection wire under variable degrees of tension that increases the radius of the distal end section.

25. The virtual electrode catheter system of claim 17, wherein the distal end section of the catheter shaft is preformed in a semicircular C-shape in an equilibrium state.

26. The virtual electrode catheter system of claim 17, wherein the second sled is operatively coupled to the actuator mechanism by a second toothed rack and a second pinion gear.

* * * * *